(12) United States Patent
Schwartz et al.

(10) Patent No.: US 11,364,105 B2
(45) Date of Patent: *Jun. 21, 2022

(54) SCAFFOLDS FOR NEURAL TISSUE AND USES THEREOF

(71) Applicant: THE TRUSTEES OF PRINCETON UNIVERSITY, Princeton, NJ (US)

(72) Inventors: Jeffrey Schwartz, Princeton, NJ (US); Jean E. Schwarzbauer, Princeton, NJ (US); Casey M. Jones, Portland, OR (US); Patrick E. Donnelly, Lawrenceville, NJ (US); Stephen B. Bandini, Newton, MA (US); Shivani Singh, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 585 days.

This patent is subject to a terminal disclaimer.

(21) Appl. No.: 15/767,616

(22) PCT Filed: Oct. 5, 2016

(86) PCT No.: PCT/US2016/055438
§ 371 (c)(1),
(2) Date: Apr. 11, 2018

(87) PCT Pub. No.: WO2017/062417
PCT Pub. Date: Apr. 13, 2017

(65) Prior Publication Data
US 2019/0380823 A1 Dec. 19, 2019

Related U.S. Application Data

(63) Continuation of application No. 14/875,168, filed on Oct. 5, 2015, now Pat. No. 10,675,138, which is a continuation-in-part of application No. 14/363,331, filed as application No. PCT/US2012/068187 on Dec. 6, 2012, now Pat. No. 10,563,160.

(60) Provisional application No. 62/060,421, filed on Oct. 6, 2014, provisional application No. 61/567,744, filed on Dec. 7, 2011.

(51) Int. Cl.
| | | |
|---|---|---|
| A61F 2/00 | (2006.01) |
| A61L 27/02 | (2006.01) |
| A61L 27/04 | (2006.01) |
| A61L 27/06 | (2006.01) |
| A61L 27/10 | (2006.01) |
| A61L 27/16 | (2006.01) |
| A61L 27/22 | (2006.01) |
| A61L 27/24 | (2006.01) |
| A61L 27/30 | (2006.01) |
| C12N 5/00 | (2006.01) |
| G01N 33/50 | (2006.01) |
| A61L 27/38 | (2006.01) |
| A61L 27/36 | (2006.01) |

(52) U.S. Cl.
CPC ............ *A61F 2/0077* (2013.01); *A61L 27/02* (2013.01); *A61L 27/047* (2013.01); *A61L 27/06* (2013.01); *A61L 27/10* (2013.01); *A61L 27/16* (2013.01); *A61L 27/227* (2013.01); *A61L 27/24* (2013.01); *A61L 27/306* (2013.01); *A61L 27/3633* (2013.01); *A61L 27/383* (2013.01); *A61L 27/3834* (2013.01); *C12N 5/0068* (2013.01); *G01N 33/5082* (2013.01); *A61F 2002/0086* (2013.01); *C12N 2533/10* (2013.01); *C12N 2533/12* (2013.01); *C12N 2533/30* (2013.01); *C12N 2533/90* (2013.01); *C12N 2535/10* (2013.01)

(58) Field of Classification Search
CPC ........... A61F 2/0077; A61F 2002/0086; A61L 27/3834; A61L 27/3633; A61L 27/02; A61L 27/047; A61L 27/383; A61L 27/227; A61L 27/24; A61L 27/10; A61L 27/06; A61L 27/306; C12N 5/0068; C12N 2533/10; C12N 2533/90; C12N 2533/12; C12N 2533/30; C12N 2535/10; G01N 33/5082

See application file for complete search history.

(56) References Cited

U.S. PATENT DOCUMENTS

| | | | |
|---|---|---|---|
| 6,645,644 B1 | 11/2003 | Schwartz et al. |
| 7,396,594 B2 | 7/2008 | Schwartz et al. |
| 7,879,456 B2 | 2/2011 | Schwartz et al. |
| 9,056,154 B2 | 6/2015 | Schwartz et al. |
| 2002/0050220 A1 | 5/2002 | Schueller et al. |
| 2002/0095219 A1 | 7/2002 | Nelles et al. |
| 2004/0096476 A1 | 5/2004 | Uhrich et al. |

(Continued)

FOREIGN PATENT DOCUMENTS

WO WO-2013086149 A1 * 6/2013 ........... A61L 27/306

OTHER PUBLICATIONS

R. Ian Freshney, "Specialized Cells." In: Culture of Animal Cell: A Manual of Basic Technique and Specialized Applications. (Hoboken, NJ, John Wiley & Sons, Inc., 2010), pp. 383-432. QH585.2.F74 2010 (Year: 2010).*

(Continued)

*Primary Examiner* — Kara D Johnson
(74) *Attorney, Agent, or Firm* — Fox Rothschild LLP

(57) ABSTRACT

The present invention provides tissue scaffolds, methods of generating such scaffolds, and methods of use of such scaffolds to generate aligned and functional neural tissues for use in methods including regenerative medicine, wound repair and transplantation.

15 Claims, 22 Drawing Sheets

(56) References Cited

U.S. PATENT DOCUMENTS

| | | |
|---|---|---|
| 2006/0085063 A1 | 4/2006 | Shastri et al. |
| 2006/0194008 A1 | 8/2006 | Schwartz et al. |
| 2008/0131709 A1 | 6/2008 | Hanson et al. |
| 2008/0299169 A1 | 12/2008 | Hoffman-Kim et al. |
| 2009/0104474 A1 | 4/2009 | Schwartz et al. |
| 2014/0330392 A1* | 11/2014 | Schwartz .............. A61L 27/306 623/23.74 |

OTHER PUBLICATIONS

Pae et al., "Attachment and growth behaviour of human gingival fibroblasts on titanium and zirconia ceramic sufaces," Biomed. Mater. (2009); 4:1-7.

Chang et al., "Modulation of neural network activity by patterning," Biosensors & Bioelectronics (2001); 16:527-533.

Viviani, Barbara, "Preparation and Coculture of Neurons and Glial Cells," Current Protocols in Cell Biology (2006) 32:2.7.1-2.7.21.

Saneinejad et al., "Patterned glass surfaces direct cell adhesion and process outgrowth of primary neurons of the central nervous system," Biomed. Mater. Res. (1998); 42(10):13-19.

Smith et al., "Dermal fibroblast and epidermal keratinocyte functionality on titania nanotube arrays," Acta Biomaterialia (2011); 7:2686-2696.

VanKooten et al., "Influence of substratum wettability on the strength of adhesion of human fibroblasts," Biomaterials (1992); 13(13):897-904.

Groth et al., "Studies on cell-biomaterial interaction: role of tyrosine phosphorylation during fibroblast spreading on surfaces varying in wettability," Biomaterials (1996); 17:1227-1234.

Teixeira et al., "Responses of human keratocytes to micro- and nanostructured substrates" J. Biomed. Mater. Res. (2004); 71A:369-376.

Evercooren, et al.: "Fibronectin Promote Rat Schwann Cell Growth and Motility", The Journal of Cell Biology, Apr. 1982, vol. 93, pp. 211-216.

Tawil, et al.: "Expression and Distribution of Fuctional Integrins in Rat CNS Glia", Journal of Neuroscience Research, 1994, vol. 39: pp. 436-447.

Sanes, et al.: "Roles of Extracellular Matrix in Neural Development", Ann. Rev. Physiol, 1983, vol. 45, pp. 581-600.

Rogers, et al.: "Selective Interaction of Peripheral and Central Nervous System Cells with Two Distinct Cell-binding Domains of Fibronectin", The Journal of Cell Biology, Sep. 1987, vol. 105, pp. 1435-1442.

Rogers, et al.: "Neuron-Specific Interactions with Two Neurite-Promoting Fragments of Fibronectin", The Journal of Neuroscience, Feb. 1985, vol. 5, No. 2, pp. 369-378.

Rogers, et al.: "Neurite Extension by Peripheral and Central Nervous System Neurons in Respone to Substratum-Bound Fibronectin and Laminin", Developmental Biology, 1983, vol. 98, pp. 212-220.

Rappa, et al.: "Efficient Expansion and Gene Transduction of Mouse Neural Stem/Progenitor Cells on Recombinant Fibronectin", Neuroscience, 2004, vol. 124, pp. 823-830.

Lallier, et al.: "Cell Lineage and Cell Migration in the Neural Crest", Part 5, Cell Biology Neuronal Migrations, and Tuberous Sclerosis, 1991, pp. 158-171.

Prestoz, et al.: "Association Between Integrin-Dependent Migration Capacity of Neural Stem Cells in Vitro and Anatomical Repair Following Transplantation", Molecular and Cellular Neuroscience, 2001, vol. 18, pp. 473-484.

Greenberg, et al.: "Role of Collagen and Fibronectin in Neural Crest Cell Adhesion and Migration", Developmental Biology, 1981, vol. 87, pp. 259-266.

Goetschy, et al.: "Fibronectin and Collagens Modulate the Proliferation and Morphology of Astroglial Cells in Culture", Int. J. Devl. Neuroscience, 1987, vol. 5, No. 1, pp. 63-70.

Dufour, et al.: "Attachment, Spreading and Locomotion of Avian Neural Crest Cells are Mediated by Multiple Adhesion Sites on Fibronectin Molecules", The EMBO Journal, 1988, vol. 7, No. 9, pp. 2661-2671.

Cardwell, et al.: "Evidence that an RGD-Dependent Receptor Mediates the Binding of Oligodendrocytes to a Novel Ligand in a Glial-Derived Matrix", The Journal of Cell Biology, Oct. 1988, vol. 107, pp. 1541-1549.

* cited by examiner

PC 12 neurites orient with matrix fibrils

Co-cultured radial glial cells and PC 12 cells align on cell-assembled ECM

SCAFFOLDS FOR NEURAL TISSUE AND USES THEREOF

CROSS-REFERENCE TO RELATED APPLICATIONS

The present application claims the benefit of priority under 35 U.S.C. 365(c) and is also a Continuation-in-Part under 35 U.S.C. 120 of U.S. patent application Ser. No. 14/875,168, filed on Oct. 5, 2015, which claims priority under 35 U.S.C. 119(e) of U.S. Provisional Application No. 62/060,421, filed on Oct. 6, 2014. The former application is also a Continuation-in-Part under 35 U.S.C. 120 of U.S. patent application Ser. No. 14/363,331, filed on Jun. 6, 2014, which is the U.S. National Phase of International Application No. PCT/US2012/068187, filed on Dec. 6, 2012, which claims the benefit of priority of U.S. Provisional Application No. 61/567,744, filed on Dec. 7, 2011. The disclosures of all of the above applications are incorporated herein by reference in their entirety.

STATEMENT REGARDING FEDERALLY SPONSORED RESEARCH OR DEVELOPMENT

This invention was made with U.S. government support under grant numbers CHE-0612572, CHE-0924104 and DMR-0819860 awarded by the National Science Foundation and grant numbers CA044627, CA160611 and GM059383 awarded by the National Institutes of Health. The U.S. government has certain rights in the invention.

BACKGROUND OF THE INVENTION

Tissue formation, wound repair, and many disease processes depend on expression and cell-mediated assembly of the appropriate extracellular matrix (ECM) proteins. In particular, oriented ECM fibers are essential for normal tissue development and homeostasis. The organization of the ECM can, however, go awry in many diseases and at sites of injury producing the unaligned collagen fibers that form in scar tissue.

A goal of regenerative medicine is to promote formation of new tissue that closely resembles the normal tissue in organization and function. Controlling cell growth in a spatially defined way enables regeneration of damaged or diseased tissues having the proper alignment of constituent cells and/or alignment of molecular complexes that the cells produce. In particular, cells direct the arrangement of ECM fibrils to correspond to their actin filaments by using cell surface receptors that are indirectly connected to the actin cytoskeleton. Therefore, a major challenge in regenerative medicine is to promote cells to assemble ECM fibrils, such as collagen, into particular orientations or alignments on a scaffold device in order to generate tissues with the required functional properties.

Many methods for controlling cell growth rely on physical patterning procedures that are not compatible with tissue scaffold device utilization. For example, grooved patterns that physically restrain cells may affect cell functions, and stamping of biologics is size and thickness limited.

SUMMARY OF THE INVENTION

The present invention is based, at least in part, on the discovery of methods for generating cell-adhesive chemical (i.e., non-biologic) patterns in nano- and micro-scale dimensions using a technique for surface-modifying solids or polymers to generate devices that have utility as bio-scaffold materials and other devices including electrodes and sensors.

The devices of the present invention can be used in, for example, regenerative medicine, wound repair, and transplant biology, as well as in screening assays to determine the effects of a test compound on living tissue by examining the effect of the test compound on various biological responses, such as for example, cell viability, cell growth, migration, differentiation and maintenance of cell phenotype.

Accordingly, in one aspect, the present invention provides patterned scaffolds for tissue. In one embodiment, the tissue scaffold comprises a base layer comprising a pattern of stripes, and an oxide layer comprising the pattern of stripes. In one embodiment the base layer and the oxide layer comprise a pattern of oxide layer stripes on the base layer.

In another embodiment, the present invention provides a tissue scaffold comprising a base layer comprising a pattern of stripes; an oxide layer comprising the pattern of stripes; and an extracellular matrix component aligned in parallel on the stripes.

In another embodiment, the tissue scaffold comprises a base layer comprising a pattern of stripes, an oxide layer comprising the pattern of stripes, and a non-biologic cell adhesive layer disposed on the oxide layer.

In another embodiment, the present invention provides a tissue scaffold comprising a base layer comprising a pattern of stripes; an oxide layer comprising the pattern of stripes; a non-biologic cell adhesive layer disposed on the oxide layer; and an extracellular matrix component aligned in parallel with the stripes.

In another embodiment, the present invention provides an artificial tissue comprising living cells attached to a tissue scaffold comprising a base layer comprising a pattern of stripes, and an oxide layer comprising the pattern of stripes.

In another embodiment, the present invention provides an artificial tissue comprising living cells attached to a tissue scaffold comprising a base layer comprising a pattern of stripes; an oxide layer comprising the pattern of stripes; and a non-biologic cell adhesive layer disposed on the oxide layer.

In another embodiment, the present invention provides an artificial tissue comprising living cells attached to a tissue scaffold comprising a base layer comprising a pattern of stripes; an oxide layer comprising the pattern of stripes; and an extracellular matrix component aligned in parallel with the stripes.

In another embodiment, the present invention provides an artificial tissue comprising living cells attached to a tissue scaffold comprising a base layer comprising a pattern of stripes; an oxide layer comprising the pattern of stripes; a non-biologic cell adhesive layer disposed on the oxide layer; and an extracellular matrix component aligned in parallel with the stripes.

In another embodiment, the present invention provides a method for making a tissue scaffold comprising: generating a pattern of stripes on a base layer by photolithography to form a substrate having a patterned base layer; and depositing an oxide layer onto the patterned base layer to form a patterned oxide layer. In another embodiment, the method for making a tissue scaffold further comprises contacting the patterned oxide layer with a non-biologic cell adhesive compound to generate a patterned cell adhesive layer.

In another embodiment, the present invention provides a method for making a tissue scaffold comprising: generating a pattern of stripes on a base layer by photolithography to form a substrate having a patterned base layer; depositing an oxide layer onto the patterned base layer to form a substrate having a patterned oxide layer; contact the substrate having the patterned oxide layer with cells and culturing under conditions suitable for the production of extracellular matrix components; and removing the cells from the substrate to provide a tissue scaffold comprising an extracellular matrix component aligned in parallel with the stripes.

In another embodiment, the present invention provides a method for making a tissue scaffold comprising: generating a pattern of stripes on a base layer by photolithography to form a substrate having a patterned base layer; depositing an oxide layer onto the patterned base layer to form a substrate having a patterned oxide layer; contacting the patterned oxide layer with a non-biologic cell adhesive compound to generate a substrate having a patterned cell adhesive layer; contacting the substrate having the patterned cell adhesive layer with cells and culturing under conditions suitable for the production of extracellular matrix components; and removing the cells from the substrate to provide a tissue scaffold comprising an extracellular matrix component aligned in parallel with the stripes.

In another embodiment, the present invention provides a method for making an artificial tissue comprising living cells attached to a tissue scaffold comprising contacting a tissue scaffold of the present invention with cells and culturing under conditions suitable for cell growth and/or differentiation.

In other embodiments, the present invention provides medical devices comprising the artificial tissues or tissue scaffolds of the invention.

In other embodiments, the present invention provides methods of tissue repair and regeneration comprising implanting the artificial tissues of the present invention in a subject in need of such tissue repair or regeneration.

In another embodiment, the present invention provides methods for identifying a compound that modulates a tissue function. The methods include providing a patterned scaffold for tissue as described herein, contacting the tissue with a test compound, and measuring the effect of the test compound on a tissue function in the presence and absence of the test compound, wherein a modulation of the tissue function in the presence of the test compound as compared to the tissue function in the absence of the test compound indicates that the test compound modulates a tissue function, thereby identifying a compound that modulates a tissue function.

In another embodiment, the present invention provides methods for identifying a compound useful for treating or preventing a tissue disease. The methods include providing a patterned scaffold for tissue as described herein, contacting the tissue with a test compound, and measuring the effect of the test compound on a tissue function in the presence and absence of the test compound, wherein a modulation of the tissue function in the presence of the test compound as compared to the tissue function in the absence of the test compound indicates that the test compound modulates a tissue function, thereby identifying a compound useful for treating or preventing a tissue disease.

In another embodiment, scaffolds for nerve tissue regeneration and methods of use thereof are provided that overcome the limitations of previous systems and methods for controlling cell alignment on polymer substrates by using cell-assembled, aligned ECM patterned polymer scaffolding that controls neurite outgrowth as opposed to the unpatterned scaffolding systems of previous inventions. The presence of aligned ECM patterns in the scaffolding systems of the present invention helps promote and coordinate neurite growth in the directions of the aligned ECM patterns. In specific embodiments of the tissue scaffold the cells are neural cells. The neural cells can be selected from the group consisting of neural stem cells, oligopotent stem cells, differentiated neurons, differentiated glial cells and neural crest cells. In some embodiments the tissue scaffold containing neural cells is co-cultured with glial support cells.

after 24 hr, and Nylon (C), PET (F), and PEEK (I) after 3 days. Cell images show actin stain, scale bar=100 μm; patterned directions in A-I are not identical with regard to the page.

Figure 8:
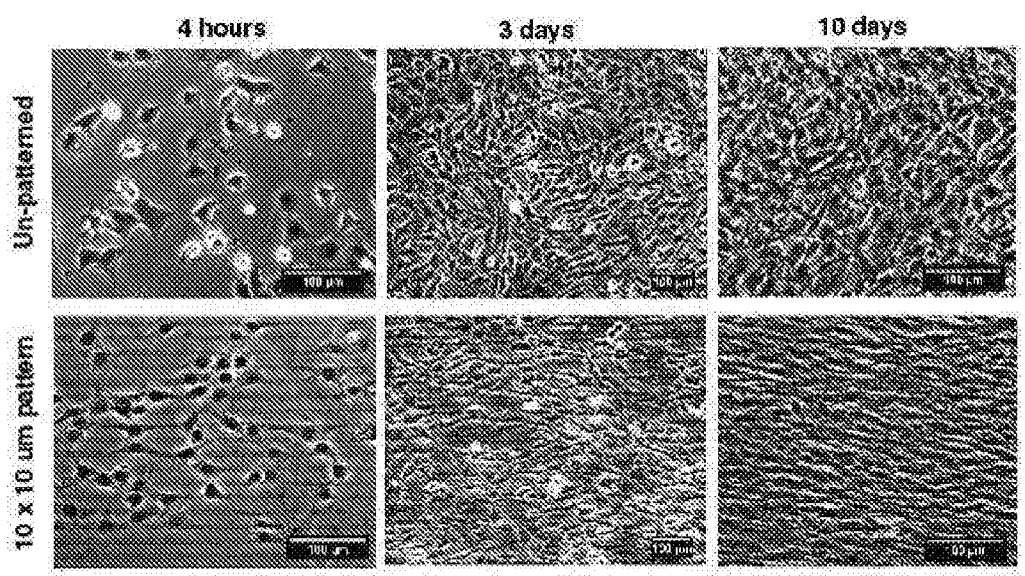

FIG. 8 shows phase contrast images of NIH3T3 cells growing on patterned and unpatterned PET.

Figure 9:
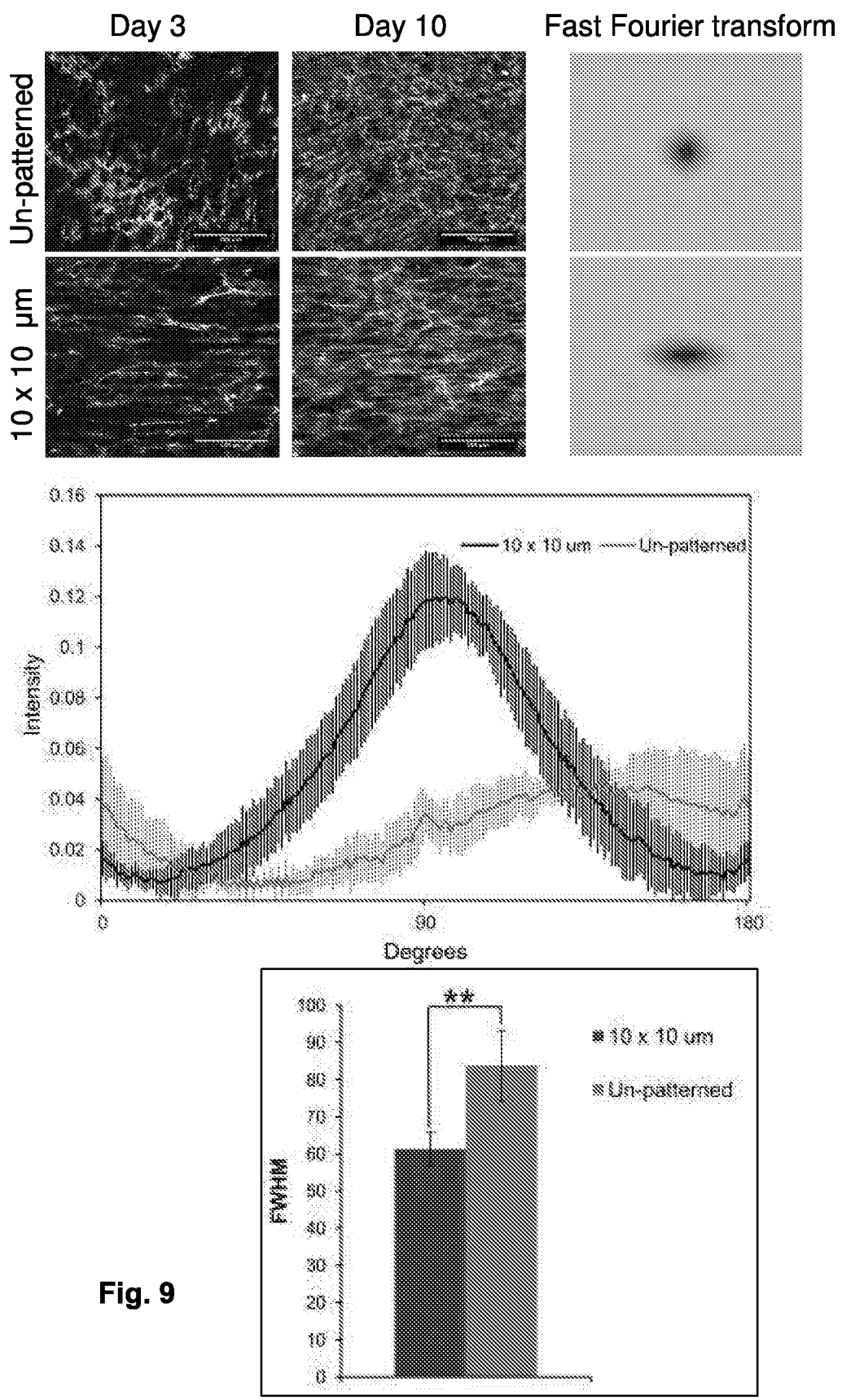

FIG. 9 shows fibronectin alignment on PET surfaces and results of fast Fourier transformation (FFT) analysis of the images of the cells confirming fibronectin alignment on the patterned PET surfaces.

Figure 10:
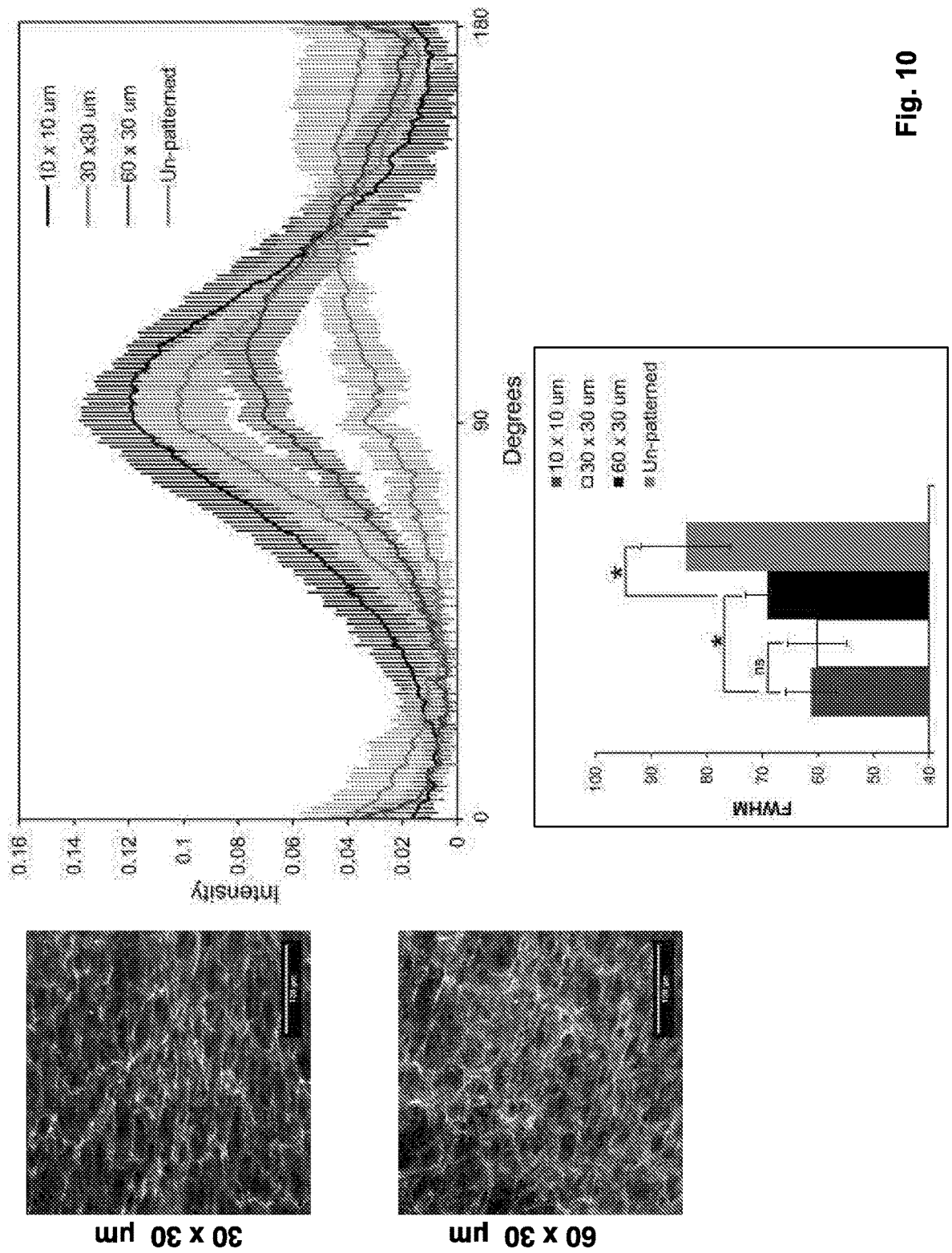

FIG. 10 shows the results of fast Fourier transformation analysis of fibronectin alignment on patterns of different dimensions.

Figure 11:
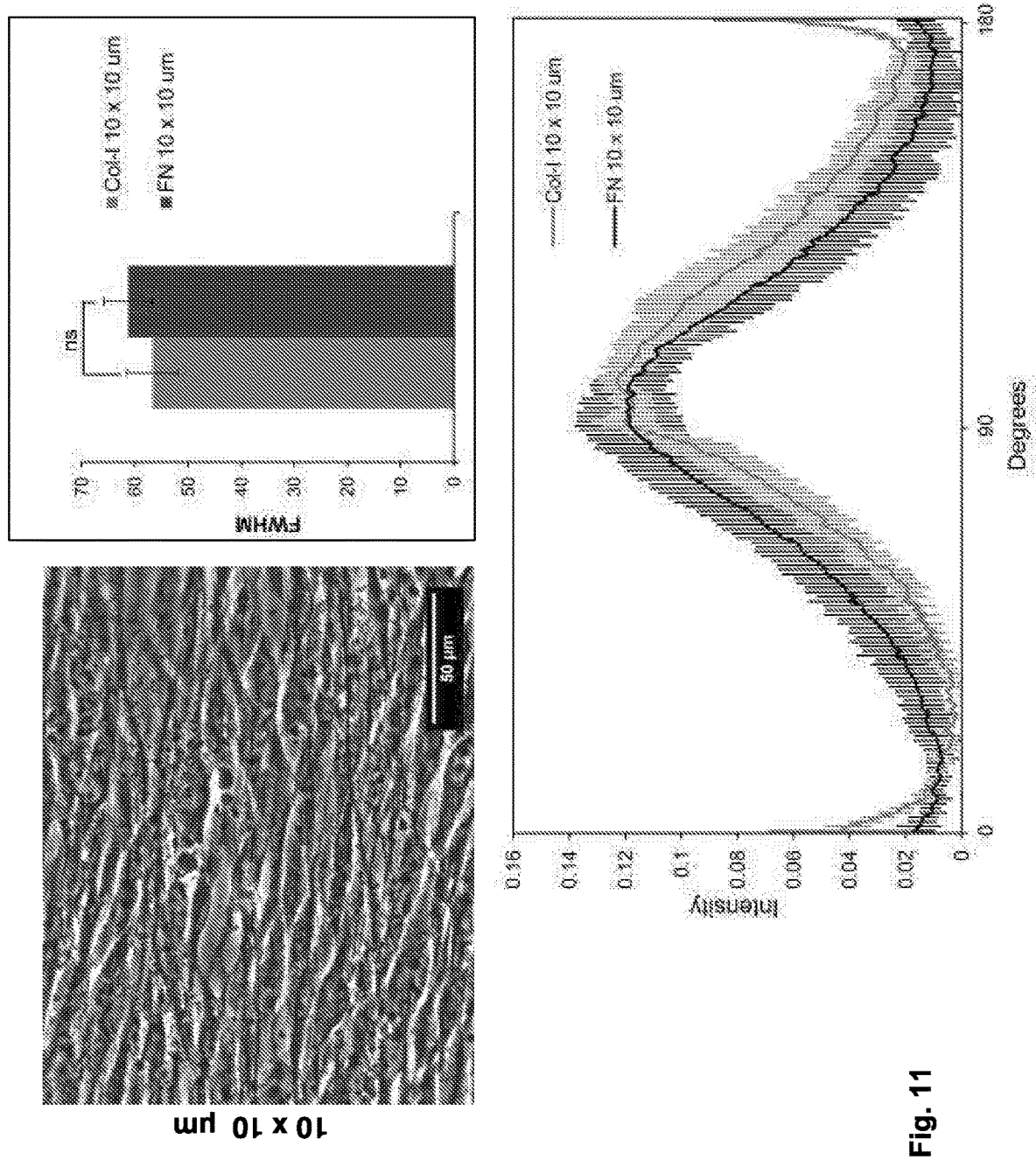

FIG. 11 shows collagen alignment on PET surfaces and results of fast Fourier transformation analysis of the images of the cells confirming collagen alignment on the patterned PET surfaces.

Figure 12:
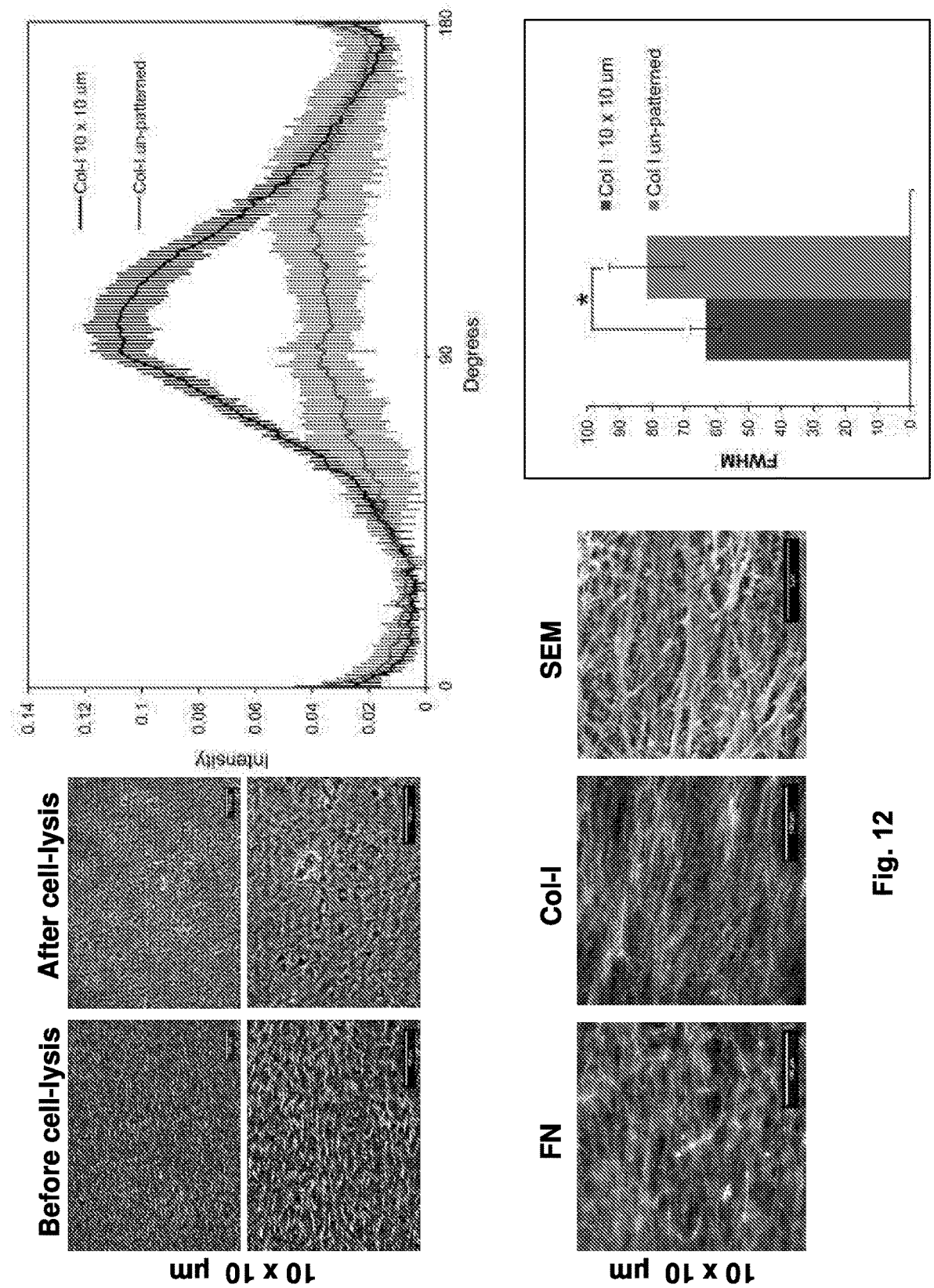

FIG. 12 shows extracellular matrix on patterned PET surfaces before and after decellularization, fibronectin (FN) alignment and collagen type I (Col-I) alignment after decellularization, and a scanning electron micrograph (SEM) of the entire matrix. The bar graph and graph show that angular alignment of collagen on the pattern is good, and that there is essentially no directionality of collagen on the unpatterned surface.

Figure 13:
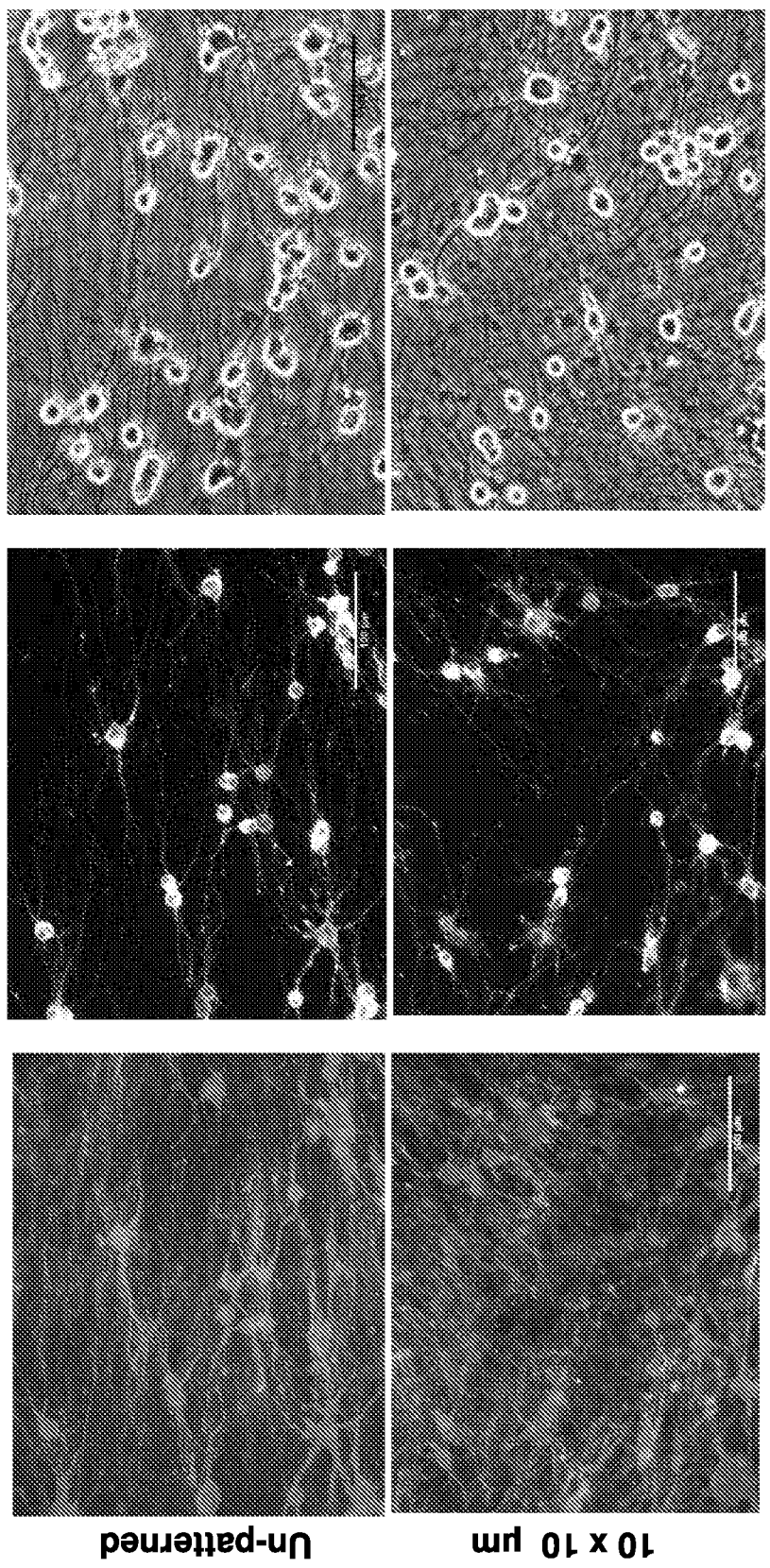

FIG. 13 shows neurites from plated PC12 cells on decellularized matrix on unpatterned (top) and patterned (bottom) surfaces. As shown, neurites aligned in the direction of collagen fibril orientation on patterned surfaces, and there was no alignment on the unpatterned control.

Figure 14:
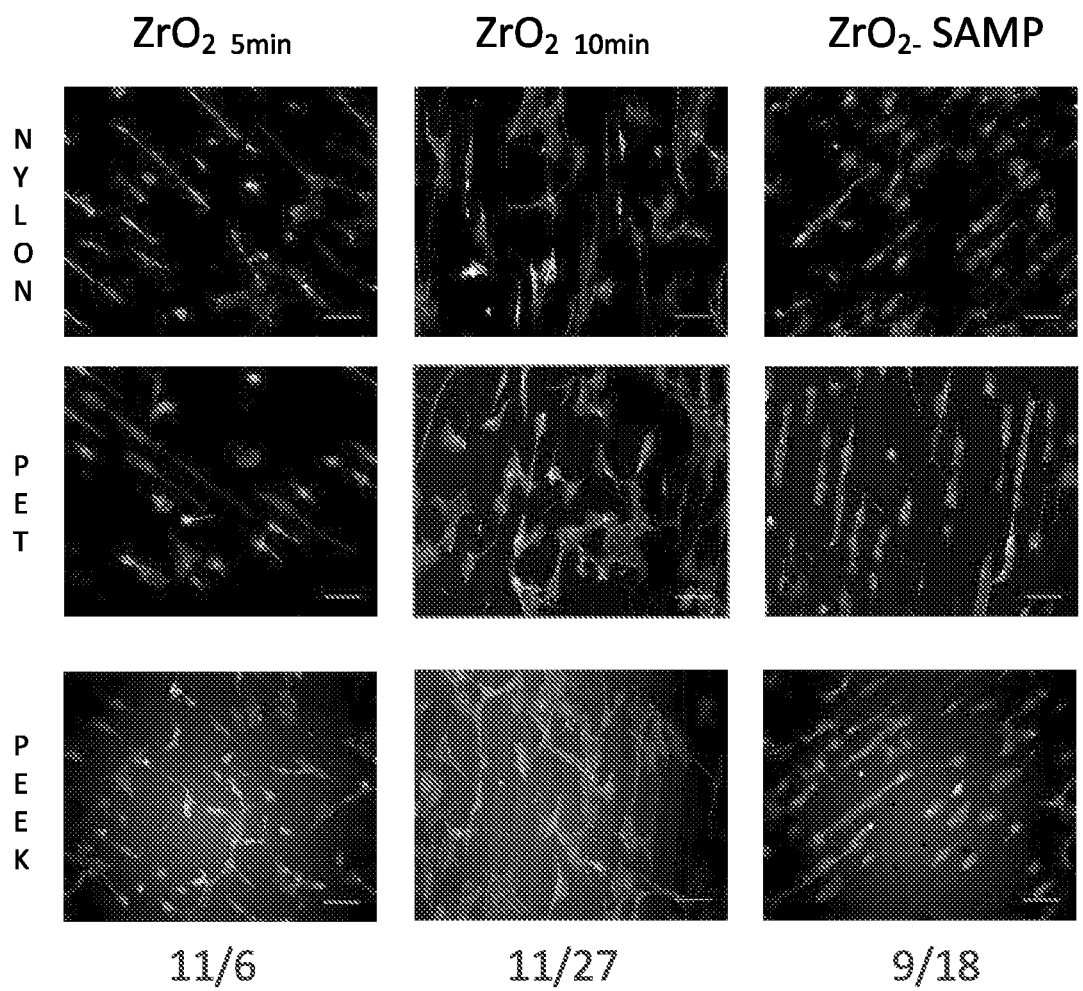

FIG. 14 shows fibroblast alignment after one day on nylon, PET and PEEK surfaces treated with ZrO2 and ZrO2/SAMP.

Figure 15:
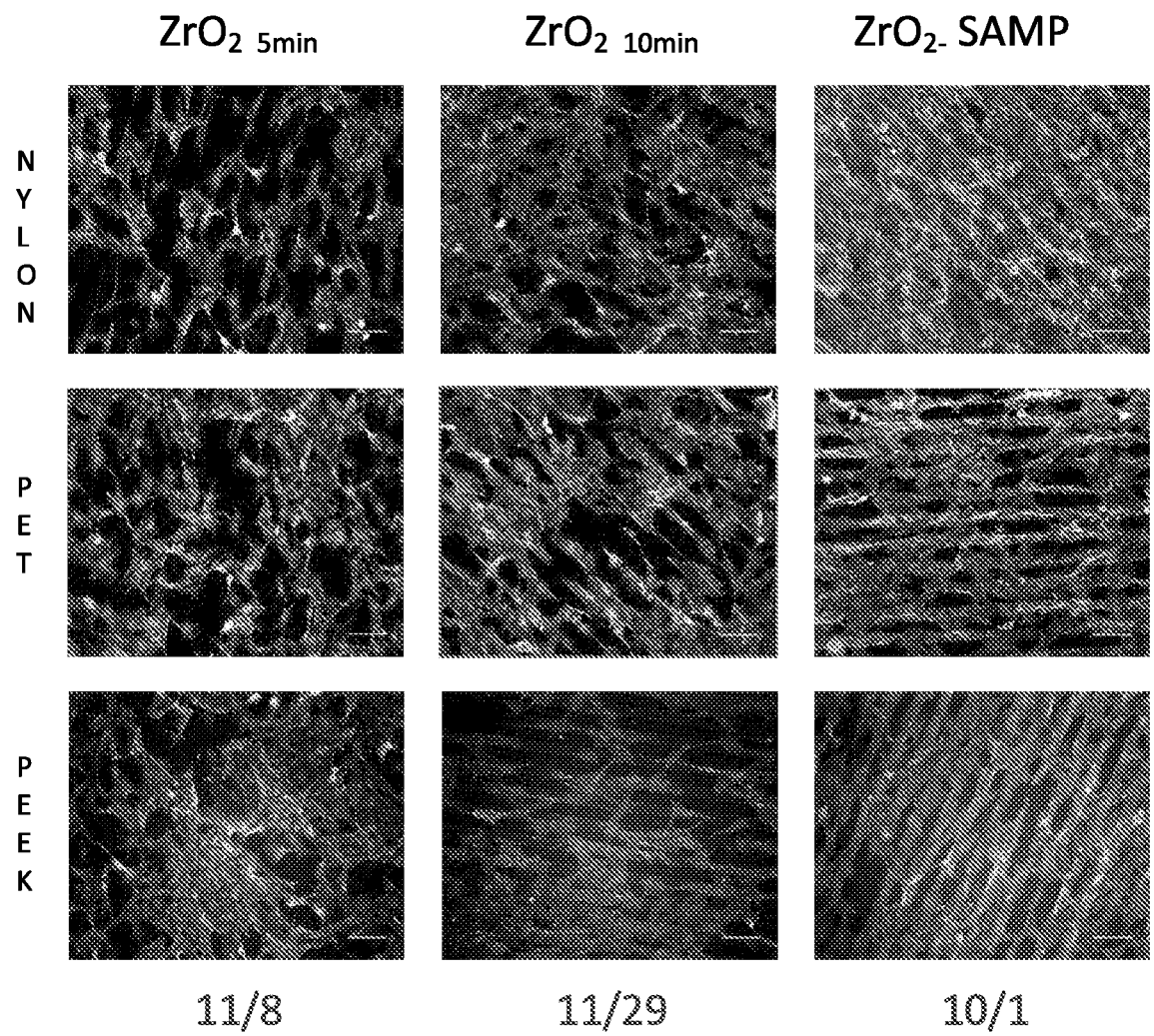

FIG. 15 shows fibroblast alignment after three days on nylon, PET and PEEK surfaces treated with ZrO2 and ZrO2/SAMP.

Figure 16:
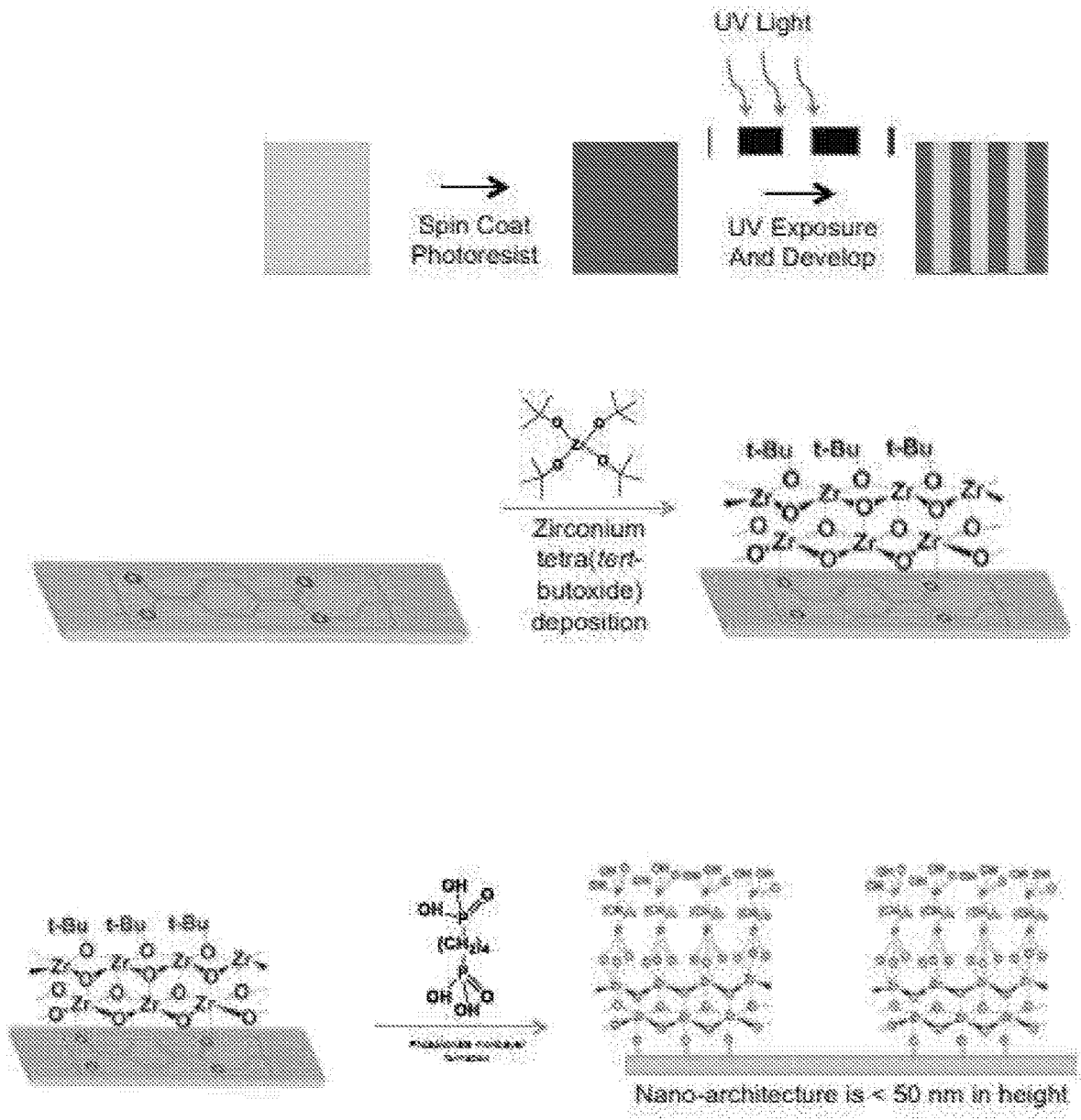

FIG. 16 represents the process by which the micropatterned polymer scaffolding base is generated, utilizing basic photolithographic techniques.

Figures 17A, 17B, 17C:
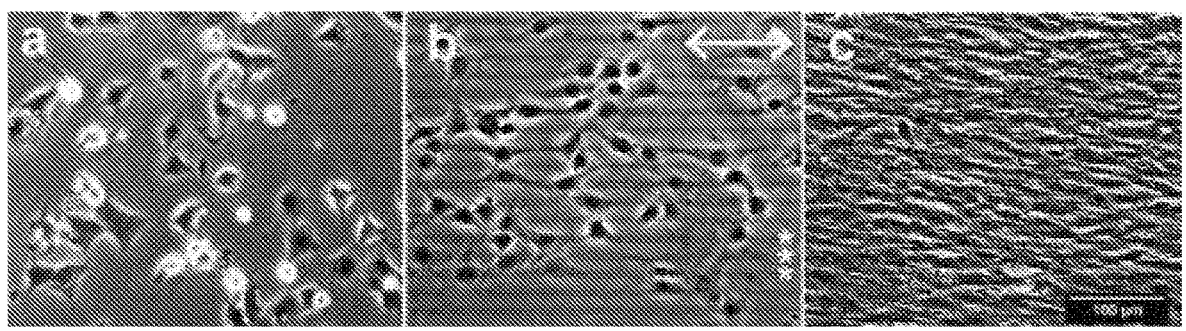

FIGS. 17A, 17B and 17C represent fibroblast alignment on the micropatterned polymer scaffolding base. NIH3T3 cells cultured on unpatterned (a) or a 10×10 μm striped pattern (b, c) were visualized by phase contrast microscopy after 4 hours (a, b) and 10 days (c). Scale bars=100 μm. Double arrow indicates the orientation of the ZrO2/SAMP pattern (in b) and the ends of several pattern stripes are indicated by asterisks (*, in b).

FIGS. 18A, 18B, 18C, 18D, 18E and 18F represent oriented assembly of ECM comprised of fibronectin and collagen fibrils. NIH 3T3 fibroblasts were grown to confluence on unpatterned (a) or 10×10 μm patterned (b, e) ZrO2/SAMP-modified PET substrates. The matrix was detected on day 10 by immunostaining with anti-fibronectin antiserum (a, b) or anti-type I collagen antibodies (e). Scale bars=100 μm. Double arrows indicate pattern orientation. Images were processed by two-dimensional FFT, and the radial summation of pixel distributions around the origin in the FFT outputs was plotted between 0° and 180° (c, f). The FWHM of each pixel intensity curve in (c) was calculated and is plotted in (d). Col-I: type I collagen; FN: fibronectin. **p<0.0005.

FIGS. 19A, 19B, 19C, 19D, 19E and 19F represent the characterization of decellularized ECM. After decellularization matrices were stained with anti-fibronectin (a) or anti-collagen type I antibodies (b) and the FFT pixel intensity distribution plots for fibronectin (FN) and type I collagen (Col-I) in this matrix are shown in (c). (d, e) Images of type I collagen fibrils in decellularized matrix on unpatterned or 10×10 μm ZrO2/SAMP patterned PET were used for FFT analysis (d) and the FWHM of these curves were determined (e). (f) SEM image of decellularized matrix. Scale bars=100 μm (a, b) and 2 μm (f). *p<0.05.

FIGS. 20A, 20B, 20C, 20D, 20E and 20F represent directional neurite outgrowth on decellularized ECM. PC12 cells were induced to extend neurites with NGF for 72 hr on unpatterned (a, c) or 10×10 μm patterned (b, d) decellularized matrix PET substrates. Cells were visualized by staining the actin cytoskeleton with rhodamine-phalloidin (a-d; red in c, d). Matrix fibrils were immunostained with anti-collagen type I antibodies (c, d; green). Double arrow indicates pattern orientation. Scale bars=100 μm. (e, f) Angles of neurites were measured relative to an arbitrary orientation for unpatterned (e) or to the pattern stripes (f) and binned in ranges of 20° centered on 90° which is parallel to the pattern. Each histogram of the angular distributions of neurites was fitted to a Gaussian to calculate the FWHM values.

Figure 21:
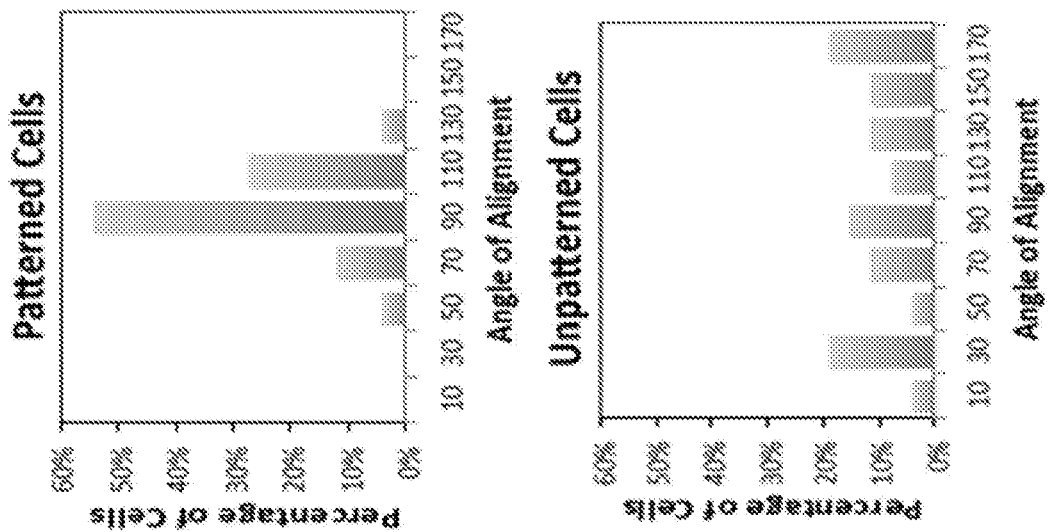
Figure 21:
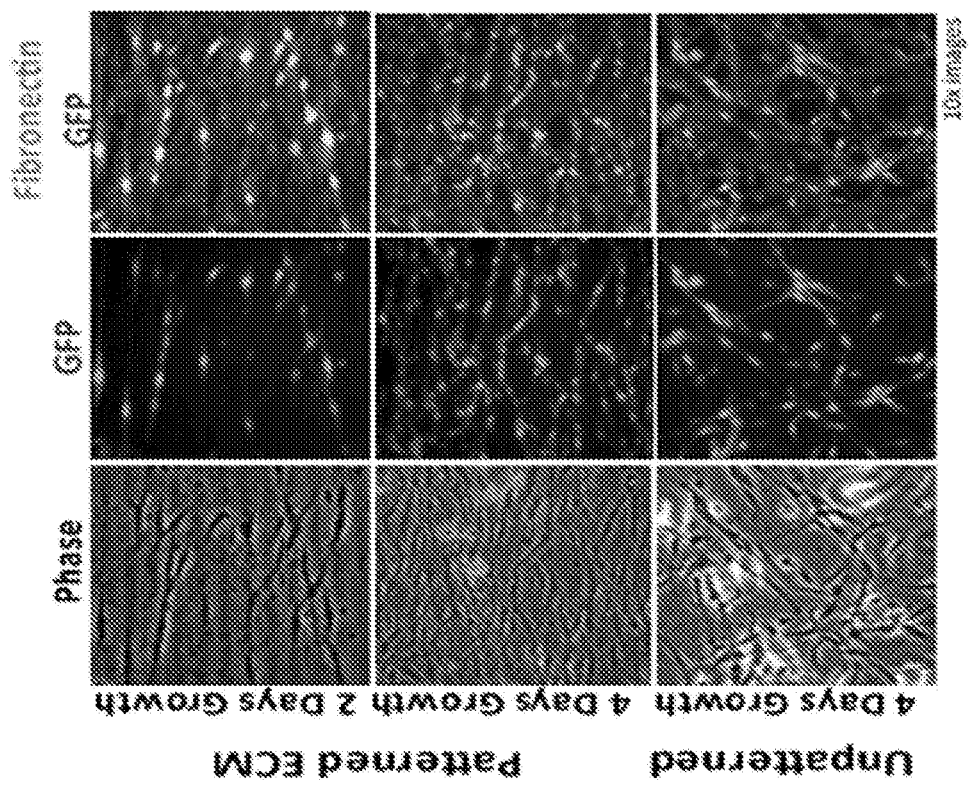

FIG. 21 represents directional radial glial cell alignment and growth. GFP-tagged radial glial cells were cultured for 2 and 4 days on ECM and was then plotted as a histogram to observe angular alignment with the ECM.

Figure 22:
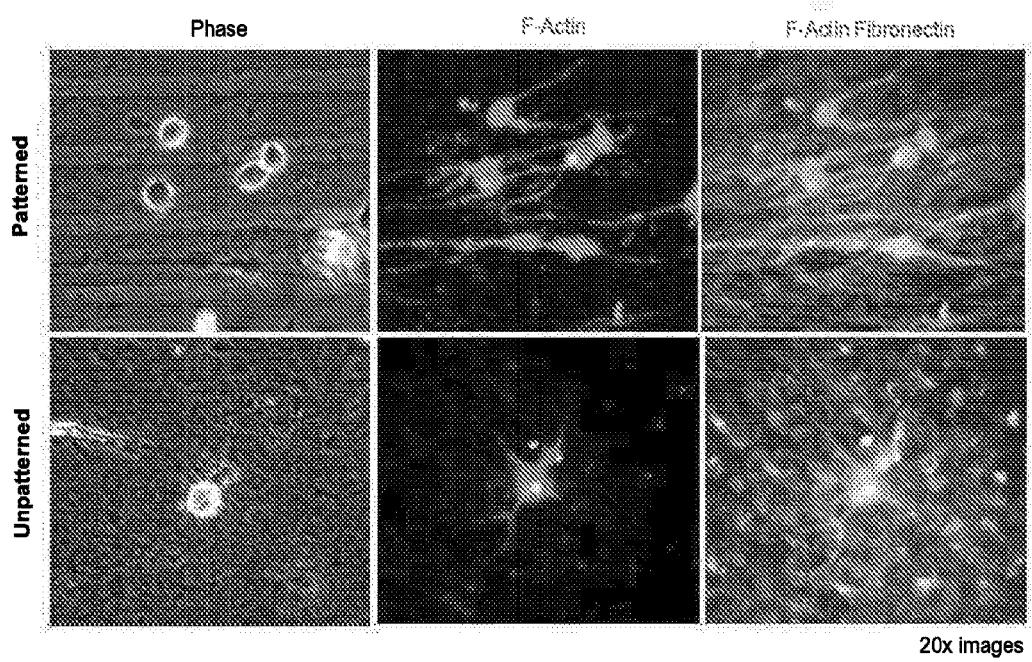
Figure 22:
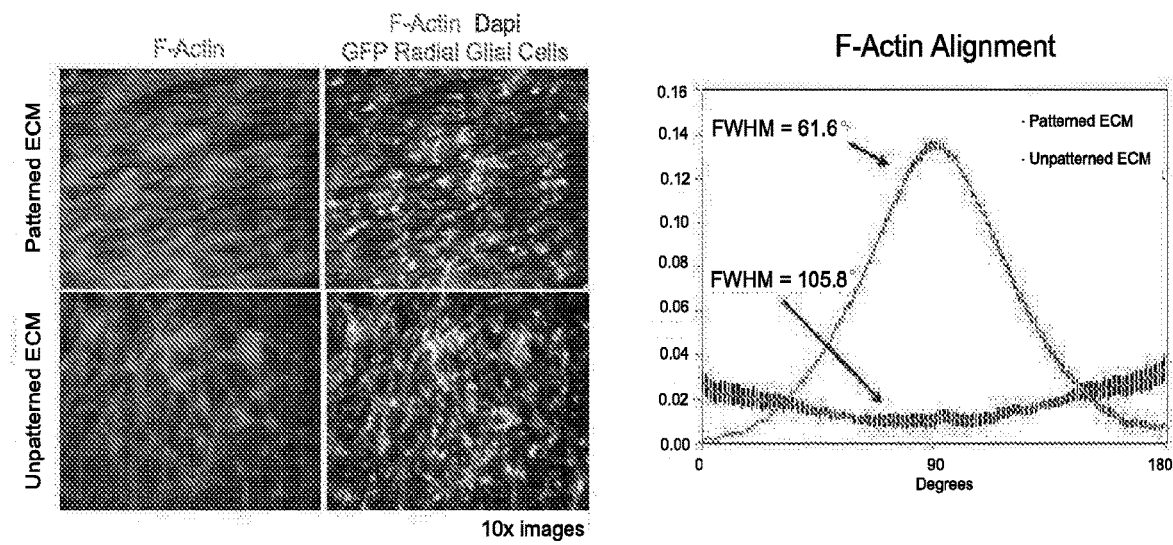

FIG. 22 represents how PC12 cells and glial cells align with ECM PC12 cells were differentiated with neural growth factor (NGF) and cultured for 3 days on decellularized ECM and stained for F-actin to observe neurite alignment. Radial glial cells were initially cultured for 2 days on ECM and PC12 cells were then seeded onto substrate and co-cultured for 3 days. FFTs were used to determine alignment of cells with FWHM highlighted for cells on unpatterned and patterned ECM.

Figures 23A, 23B:
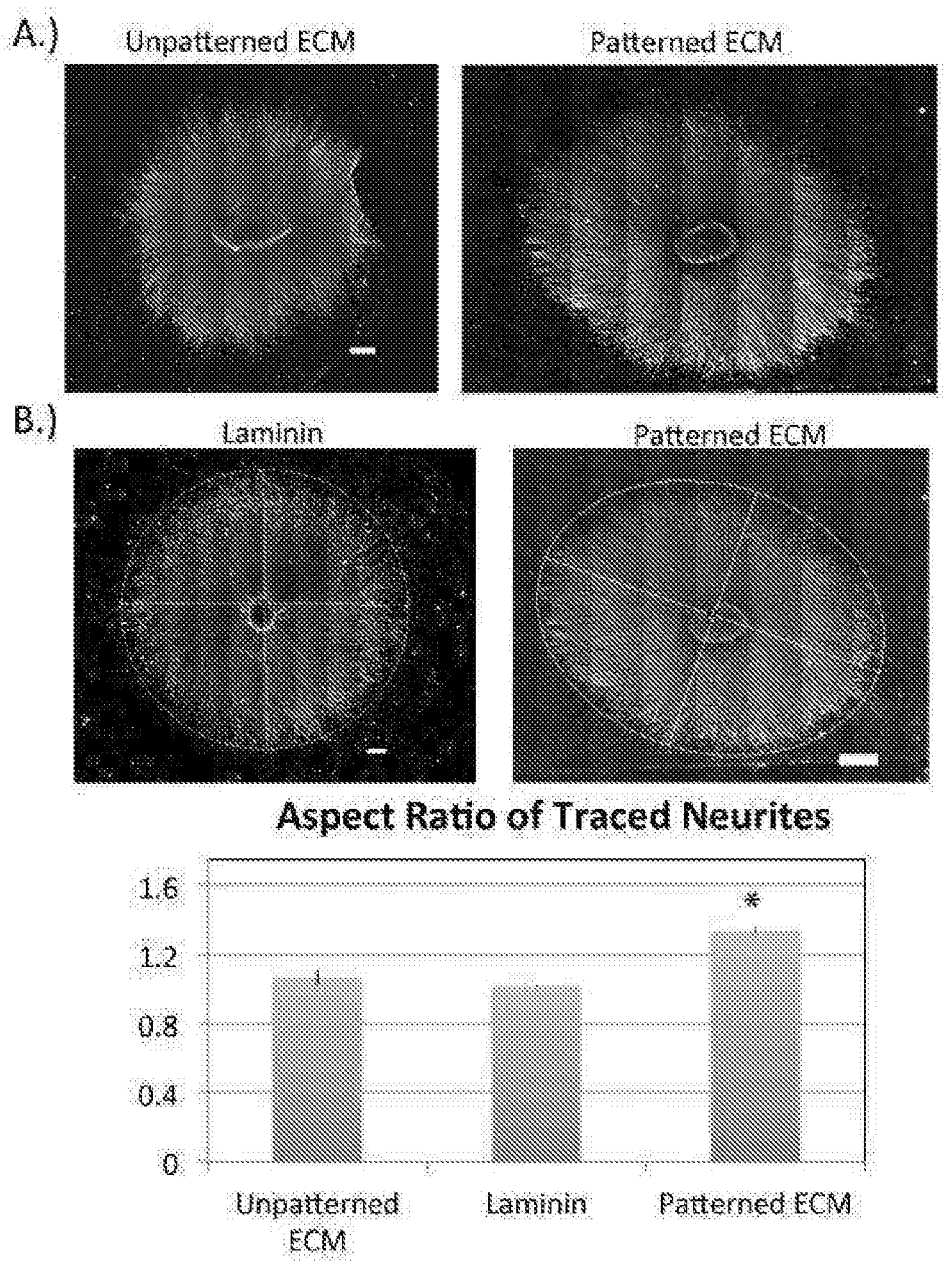

FIGS. 23A and 23B demonstrate neurite outgrowth and directionality using sympathetic cervical ganglia. Substrates included a glass coverslip coated with a 10 μg/ml solution of laminin (Laminin), decellularized fibroblast ECM on an unpatterned glass coverslip (Unpatterned ECM), and decellularized aligned ECM on a 20 μm×20 μm patterned PET surface (Patterned ECM). A single ganglion with extended neurites is shown in each image (FIGS. 23A and 23B). The substrate is indicated above the image. Scale bar=500 μm. In FIG. 23A neurite outgrowth was fitted with an ellipse (lines on images) to determine if neurite extension deviated from circular. The aspect ratios (long axis divided by the short axis) displayed in the graph were calculated and averaged for a minimum of 3 samples per condition. The asterisk (*) indicates that the aspect ratio on patterned ECM is significantly different from the other substrates.

DETAILED DESCRIPTION OF THE INVENTION

The present invention is based, at least in part, on the discovery of methods for generating cell-adhesive chemical (i.e., non-biologic) patterns in nano- and micro-scale dimensions using a technique for surface-modifying solids or polymers to prepare devices that have utility as bio-scaffold materials, electrodes, sensors or other devices.

The devices and methods of the present invention are simpler than previously described methods and devices in that it is not necessary to provide a biologic cell adhesion molecule, such as an RGD peptide, to mimic an in vivo environment to properly align and/or orient cells to form a functional tissue in vitro with appropriate cellular organization and biological activities. In other words, it is not necessary to functionalize the chemical layer to elicit a biological response using a material such as a saccharide, an oligosaccharide, a polysaccharide, a nucleic acid, a protein and/or a peptide. The lack of biologic cell-adhesive materials prevents encumbrance of cell receptors that may be involved in cell spreading and extracellular interactions affecting cellular organization and tissue alignment. Further, the patterns do not affect the physical properties of the substrate. The devices and methods of making the devices of the present invention are also simpler than previously described methods and devices in that they can be performed in about one hour and the base layer used to generate the scaffolds does not need to comprise a reactive side-chain-containing species.

In the devices and methods of the present invention, the patterns are more cell-adhesive than the substrates on which the patterns are developed. Cells attach to the patterns but are not constrained into the patterns by physical means. As the cells proliferate, they align into unmodified areas of the patterns to form confluent monolayers of cells while maintaining pattern alignment across the substrate surface.

Accordingly, described herein are methods and devices which may be used in a broad range of applications, for example, in regenerative medicine, wound repair, transplant biology, drug delivery, testing the effect of substances upon cells, tissue formation, cell actuation, and developmental biology.

Furthermore, the methods described herein are amenable to a wide variety of hard or soft surfaces, including soft polymeric surfaces.

I. Devices of the Invention and Methods of Production of the Same

Accordingly, in one aspect, the present invention provides patterned scaffolds for tissue. In one embodiment, the present invention provides a tissue scaffold comprising a base layer comprising a pattern of stripes, and an oxide layer comprising the pattern of stripes. In another embodiment, the tissue scaffold comprises a base layer comprising a pattern of stripes, an oxide layer comprising the pattern of stripes, and a non-biologic cell adhesive layer disposed on the oxide layer.

A base layer for use in the present invention may be a solid, rigid, or hard polymeric surface, a semi-rigid polymeric surface, a soft polymeric surface, a hard non-polymeric surface, a semi-rigid non-polymeric surface, or a soft non-polymeric surface. In, one embodiment, a base layer is biologically inert. In one embodiment, a base layer comprises two or more surfaces. For example, a base layer comprising a soft polymeric or non-polymeric surface may be placed temporarily on a solid or semi-rigid polymeric or non-polymeric surface.

In some embodiments, a base layer for use in the compositions and methods of the invention may have a Young's modulus of about 0.001-0.1, 0.005-0.2, 0.005-0.5, 0.05-1.0, 0.075-1.0, 0.1-2.0, 1.0-2.0, 1.5-5.0, 2.0-5.0, 3.0-7.0, 3.0-10, 5.0-15, 5.0-20, 10-20, 15-30, 20-30, 25-50, 30-50, 50-75, 50-100, 75-125, 100-150, 125-150, 150-200, 175-200, 200-250, or about 250-300 gigapascals (GPa). Ranges and values intermediate to the above recited ranges and values are also contemplated to be part of the invention. For example, a Young's modulus of about 6.5-9.8, or 5.2-7.8 GPa is intended to be encompassed by the present invention.

In other embodiments, a base layer for use in the compositions and methods of the invention may have a Young's modulus of about 0.001-0.1, 0.005-0.2, 0.005-0.5, 0.05-1.0, 0.075-1.0, 0.1-2.0, 1.0-2.0, 1.5-5.0, 2.0-5.0, 3.0-7.0, 3.0-10, 5.0-15, 5.0-20, 10-20, 15-30, 20-30, 25-50, 30-50, 50-75, 50-100, 75-125, 100-150, 125-150, 150-200, 175-200, 200-250, or about 250-300 kilopascals (kPa). Ranges and values intermediate to the above recited ranges and values are also contemplated to be part of the invention. For example, a Young's modulus of about 6.5-9.8, or 5.2-7.8 kPa is intended to be encompassed by the present invention. For nerve regeneration, a lower Young's modulus may be used.

In one embodiment, the base layer is selected from the group consisting of a hard polymeric surface, a semi-rigid polymeric surface, and a soft polymeric surface, a hard non-polymeric surface, a semi-rigid non-polymeric surface, and a soft non-polymeric surface. In one embodiment, the base layer comprises a polyamide, a polyamide hydrogel, a polyurethane, a polyurea, a polyester, a polyester hydrogel, a polyketone, a polyimide, a polysulfide, a polysulfoxide, a polysulfone, a polythiophene, a polypyridine, a polypyrrole, polyethers, silicone (polysiloxane), polysaccharides, fluoropolymers, epoxies, aramides, amides, imides, polypeptides, polyethylene, polystyrene, polypropylene, glass reinforced epoxies, liquid crystal polymers, thermoplastics, bismaleimide-triazine (BT) resins, benzocyclobutene ABFGx13, low coefficient of thermal expansion (CTE) films of glass and epoxies, polyvinyls, polyacrylics, polyacrylates, polycarbonates, polytetrafluoroethylene (PTFE), polyethylene terephthalate (PET), quartz, silicon (e.g., silicon wafers), glass, ceramic, metals and metal alloys including titanium, titanium alloys, tantalum, zirconium, stainless steel and cobalt-chromium alloys, metal oxides, poly(vinyl pyrrolidone), poly(-hydroxyethyl methacrylate), poly(N-vinyl pyrrolidone), poly(methyl methacrylate), poly(vinyl alcohol), poly(acrylic acid), polyacrylamide, polyacrylamide hydrogels, polyrethylene-co-vinyl acetate), poly(ethylene glycol), poly(methacrylic acid), polylactides (PLA), polyglycolides (PGA), poly(lactide-co-glycolides) (PLGA), polylactones, polylactone hydrogels, polyanhydrides, polyphosphazenes, polygermanes, polyorthoesters, polyolefins, poly-carbonates, biopolymers, such as a silk, collagen, copolymers and derivatives thereof, and composites including these polymers. In one preferred embodiment, the base layer is silicon, polyetheretherketone, nylon, including nylon 6,6 or PET. In another preferred embodiment, the base layer is silicone or polyacrylamide. In other preferred embodiments the base layer is hydrophilic polyacrylamide, hydrophilic polyester, polyacrylamide hydrogel, polyester hydrogel or polylactone hydrogel. In another preferred embodiment, the base layer is silk or collagen. In another preferred embodiment, the base layer is titanium or stainless steel.

In one embodiment, the base layer is a support structure.

In one embodiment, the support structure is selected from the group consisting of a Petri dish, a cover-slip, a glass slide, a multi-well plate, a microfluidic chamber, an implant, and a medical device.

Medical devices for use as base layers in the present invention include, for example, diagnostic implant devices, biosensors, stimulators, neural stimulators, neural activity recorders, diabetic implants such as glucose monitoring devices, external fixation devices, external fixation implants, orthopedic trauma implants, implants for use in joint and spinal disorders/reconstruction such as plates, screws, rods, plugs, cages, scaffolds, artificial joints (e.g., hand, wrist, elbow, shoulder, spine, hip, knee, ankle), wires and the like, oncology related bone and soft tissue replacement devices, dental and oral/maxillo-facial devices, cardiovascular implants such as stents, catheters, valves, rings, implantable defibrillators, and the like, contact lenses, ocular implants, keratoprostheses, dermatologic implants, cosmetic implants, implantable medication delivery pumps; general surgery devices and implants such as but not limited to drainage catheters, shunts, tapes, meshes, ropes, cables, wires, sutures, skin staples, burn sheets, and vascular patches; and temporary or non-permanent implants.

The base layer comprises a pattern of stripes having at least two parallel stripes wherein adjacent stripes are separated by a space. In one embodiment, the width and spacing of the stripes is about 0.1 µm to about 1000 µm.

The width and spacing of the stripes may be varied over the range from about 0.1 µm to about 1000 µm, from about 1 µm to about 500 µm, from about 1 µm to 250 µm, from about 1 µm to 160 µm, from about 1 µm to 100 µm, from about 1 µm to 90 µm, from about 1 µm to 80 µm, from about 1 µm to 70 µm, from about 1 µm to 60 µm, from about 1 µm to 50 µm, from about 1 µm to 40 µm, from about 1 µm to 30 µm, from about 1 µm to 20 µm, from about 1 µm to 10 µm about 2 µm to 100 µm, from about 2 µm to 90 µm, from about 2 µm to 80 µm, from about 2 µm to 70 µm, from about 2 µm to 60 µm, from about 2 µm to 50 µm, from about 2 µm to 40 µm, from about 2 µm to 30 µm, from about 2 µm to 20 µm, from about 2 µm to 10 µm, from about 1 µm to 100 µm, from about 5 µm to about 160 µm, from about 5 µm to about 100 µm, from about 5 µm to about 90 µm, from about 5 µm to about 80 µm, from about 5 µm to about 70 µm, from about 5 µm to about 60 µm, from about 5 µm to about 50 µm, from about 5 µm to about 40 µm, from about 5 µm to about 30 µm, from about 5 µm to about 20 µm, and from about 5 µm to about 10 µm. Ranges and values intermediate to the above recited ranges and values are also contemplated to be part of the invention. For example, a width and spacing of about 4-28, or 7-19 µm are intended to be encompassed by the present invention.

The width and spacing of the stripes can be equivalent or different. For example, both the width and spacing can be about 0.1, about 0.2, about 0.25, about 0.5, about 0.75, about 1, about 2, about 3, about 4, about 5, about 6, about 7, about 8, about 9, about 10, about 11, about 12, about 13, about 14, about 5, about 16, about 17, about 18, about 19, or about 20 µm. In other embodiments, the width can be about 0.1, about 0.2, about 0.25, about 0.5, about 0.75, about 1, about 2, about 3, about 4, about 5, about 6, about 7, about 8, about 9, about 10 µm, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 µm, and the spacing can be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 µm. Values intermediate to the above recited values are also contemplated to be part of the invention. For example, a width and spacing of about 5.6 or 23.1 µm are intended to be encompassed by the present invention.

In one preferred embodiment, the stripes are about 5 µm to 100 µm wide and spaced about 5 µm to 100 µm apart. In another preferred embodiment, the stripes are about 5 µm wide and spaced about 5 µm apart. In another preferred embodiment, the stripes are about 10 µm wide and spaced about 10 µm apart. In another preferred embodiment, the stripes are about 20 µm wide and spaced about 20 µm apart. In yet another preferred embodiment, the stripes are about 30 µm wide and spaced about 30 µm apart. In yet another preferred embodiment, the stripes are about 20 µm wide and spaced about 10 µm apart.

An oxide for use in the oxide layer of the scaffold on the present invention includes any compound(s) that when contacted with the patterned base layer forms a continuous layer on the patterned base layer. In one embodiment, the oxide is a metal oxide, e.g., formed from an alkoxide precursor. In one embodiment the alkoxide is of a transition metal. Periodic Table Group 3-6 and 13-14 metals are transition metals suitable for use in the present invention. Such metals include Zr, Al, Ti, Hf, Ta, Nb, V and Sn. Depending upon the position of the transition metal on the Periodic Table, a transition metal alkoxide will have from three to six alkoxide groups or a mixture of oxo and alkoxide groups. In one embodiment, an alkoxide group has from 2 to 4 carbon atoms, and includes, for example, ethoxide, propoxide, iso-propoxide, butoxide, iso-butoxide, tert-butoxide and fluoronated alkoxide. In one embodiment, a metal alkoxide for use in the present invention is zirconium tetra(tert-butoxide). In another embodiment, a metal alkoxide for use in the present invention is tantalum pentaethoxide. Suitable oxides for use in the present invention also include those described in U.S. Patent Publication No. 2009/0104474 and PCT Publication No. WO 2009/052352, the entire contents of each of which are incorporated herein by reference. In one preferred embodiment, the oxide layer comprises a metal oxide. In another preferred embodiment, the metal oxide is formed from the precursor zirconium tetra(tert-butoxide).

For embodiments in which a non-biologic cell adhesive layer is disposed on the oxide layer, the cell adhesive layer comprises an adhesive chemical compound. A cell adhesive chemical compound is any organic compound that is sufficiently reactive to react with the oxide layer, e.g., sufficiently reactive with a metal oxide or alkoxide, such as, for example, an organic compound comprising a phosphonic, carboxylic, sulfonic, phosphinic, phosphoric, sulfinic, or hydroxamic acid group. In one preferred embodiment, the cell adhesive layer comprises a phosphonate.

In certain embodiments, the scaffolds further comprise living cells. It has been discovered in accordance with the present invention that cells can adhere to the patterned oxide layers in the absence of a cell adhesive layer disposed on the oxide layer.

Accordingly, in one embodiment, the present invention provides an artificial tissue comprising living cells attached to a tissue scaffold comprising a base layer comprising a pattern of stripes, and an oxide layer comprising the pattern of stripes. In another embodiment, the present invention provides an artificial tissue comprising living cells attached to a tissue scaffold comprising: a base layer comprising a pattern of stripes; an oxide layer comprising the pattern of stripes; and a non-biologic cell adhesive layer disposed on the oxide layer. The type of cells is not limited, and includes, for example, fibroblasts, endothelial cells, keratinocytes, osteoblasts, chondroblasts and chondrocytes, hepatocytes, macrophages, cardiac muscle cells, smooth muscle cells, skeletal muscle cells, tendon cells, ligament cells, neural cells, epithelial cells, and stem cells. Stem cells include embryonic stem cells, adult stem cells, and induced pluripotent stem cells. In one preferred embodiment, the cells are mesenchymal stem cells. In another preferred embodiment, the cells are human cells.

In another embodiment, the present invention provides a tissue scaffold comprising: a base layer comprising a pattern of stripes; an oxide layer comprising the pattern of stripes; and an extracellular matrix component aligned in parallel with the stripes. In another embodiment, the present invention provides a tissue scaffold comprising: a base layer comprising a pattern of stripes; an oxide layer comprising the pattern of stripes; a non-biologic cell adhesive layer disposed on the oxide layer; and an extracellular matrix component aligned in parallel with the stripes. Extracellular matrix components are known in the art and include for example, fibronectin and collagens.

The scaffolds comprising an extracellular matrix component may further comprise living cells attached to the matrix component. Accordingly, in another embodiment, the present invention provides an artificial tissue comprising living cells attached to a tissue scaffold comprising: a base layer comprising a pattern of stripes; an oxide layer comprising the pattern of stripes; and an extracellular matrix component aligned in parallel with the stripes. In another embodiment, the present invention provides an artificial tissue comprising living cells attached to a tissue scaffold comprising: a base layer comprising a pattern of stripes; an oxide layer comprising the pattern of stripes; a non-biologic cell adhesive layer disposed on the oxide layer; and an extracellular matrix component aligned in parallel with the stripes. The type of cells is not limited, and includes, for example, fibroblasts, endothelial cells, keratinocytes, osteoblasts, chondroblasts and chondrocytes, hepatocytes, macrophages, cardiac muscle cells, smooth muscle cells, skeletal muscle cells, tendon cells, ligament cells, neural cells, epithelial cells, and stem cells. Stem cells include embryonic stem cells, adult stem cells, and induced pluripotent stem cells. In one preferred embodiment, the cells are mesenchymal stem cells. In another preferred embodiment, the cells are human cells. The cells need not be the same cells used to produce the extracellular matrix component on the substrate. The cells may be obtained from a subject to be treated with the artificial tissue generated on the substrate.

In another embodiment, the present invention provides a method for making a tissue scaffold comprising: generating a pattern of stripes on a base layer by photolithography to form a patterned base layer; and depositing an oxide layer onto the patterned base layer to form a patterned oxide layer. In another embodiment, the method for making a tissue scaffold further comprises contacting the patterned oxide layer with a non-biologic cell adhesive compound to generate a patterned cell adhesive layer.

Methods of photolithography known in the art may be used to form the patterned base layer. For example, the method may comprise depositing a photoresist onto the base layer, thereby generating a photoresist layer, placing a mask on top of the photoresist layer and exposing the photoresist layer to ultraviolet radiation, thereby generating a patterned base layer.

As used herein, the term "depositing" refers to a process of placing or applying an item or substance onto another item or substance (which may be identical to, similar to, or dissimilar to the first item or substance). Depositing may include, but is not limited to, methods of using spraying, dip casting, spin coating, evaporative methods, sputter methods, immersion methods, extractive deposition methods, or other methods to associate the items or substances. The term depositing includes applying the item or substance to substantially the entire surface as well as applying the item or substance to a portion of the surface.

In one embodiment, spin coating is used to apply a photoresist layer onto the base layer. Spin coating is a process wherein the base layer is, for example, mounted to a chuck under vacuum and is rotated to spin the base layer about its axis of symmetry and a liquid or semi-liquid substance, e.g., a photoresist, is dripped onto the base layer, with the centrifugal force generated by the spin causing the liquid or semi-liquid substance to spread substantially evenly across the surface of the base layer. Variations of this process, for example coating and then spinning, or spinning and then dripping, may also be used.

"Photoresist" is any substance that is sensitive to ultraviolet radiation, e.g., wave-lengths of light in the ultraviolet or shorter spectrum (<400 nm). A photoresist may be positive or negative. Suitable photoresists include, without limitation, AZ-5412E, AZ-701, AZ-1505, AZ-1518, and AZ-4330 (all are available from AZ Electronic Materials). In one embodiment the photoresist is AZ-5412E.

A base layer comprising a photoresist may be patterned by providing a mask comprising the desired shape and/or pattern, i.e., a striped pattern. The mask may be a solid mask such as a photolithographic mask. The mask is provided and placed on top of the photoresist layer. Subsequently, a portion of the photoresist layer (i.e., the portion of the photoresist not covered by the mask) is exposed to ultraviolet radiation.

The mask placed on top of the photoresist layer is typically fabricated by standard photolithographic procedure, e.g., by means of electron beam lithography. Other methods for creating such masks include focused energy for ablation (micromachining) including lasers, electron beams and focused ion beams. Similarly, chemical etchants may be used to erode materials through the photoresist when using an alternative mask material. Examples of chemical etchants include hydrofluoric acid and hydrochloric acid. Photolithographic masks are also commercially available.

Any suitable material, e.g., a material that has a flat surface, e.g., a metal (gold, silver, platinum, tantalum, or aluminum), a ceramic (alumina, titanium oxide, silica, or silicon nitride), may be used for making the mask.

In some embodiments, a combination of positive and negative photoresists can be used. For example, a positive photoresist is deposited on a base layer in a particular pattern and subsequently a negative photoresist in a complementary pattern is applied. This results in a patterned tissue scaffold that comprises a pattern that comprises regions that are more cell adhesive next to regions that are less cell-adhesive.

Once the photoresist layer is exposed to ultraviolet radiation and a patterned base layer is formed, the mask is removed and an oxide is deposited to the patterned base layer to form a patterned oxide layer. The oxide binds directly onto the base layer and does not depend on the introduction of reactive side chain-containing species into the polymeric base layer.

One embodiment of the invention encompasses a method for making a tissue scaffold comprising the steps of generating a pattern on a base layer of protective photoresist compound stripes and unprotected base layer stripes using photolithography, to form a patterned base layer; and depositing an oxide layer onto the unprotected stripes to form a patterned oxide layer.

In one embodiment, a thin oxide layer, e.g., a metal oxide, is deposited onto the patterned base layer as a continuous layer. As used herein, the term "continuous layer" is a layer that is formed by a matrix of individual molecules that are chemically bonded and linked to each other, as opposed to individual molecules covering the surface. In the present case, in one embodiment, oxide molecules, e.g., metal oxide molecules, are bonded together on at least a portion of the patterned base layer to form a continuous layer. In another embodiment, a thin oxide layer, e.g., a metal oxide, is deposited onto the patterned base layer as a non-continuous layer, i.e., a pattern of individual molecules covering the surface.

An oxide for use in the oxide layer of the scaffold on the present invention includes any compound(s) that when contacted with the patterned base layer forms a continuous layer on the patterned base layer. In one embodiment, the oxide is a metal oxide, e.g., formed from an alkoxide precursor. In one embodiment the alkoxide is of a transition metal. Periodic Table Group 3-6 and 13-14 metals are transition metals suitable for use in the present invention. Such metals include Zr, Al, Ti, Hf, Ta, Nb, V and Sn. Depending upon the position of the transition metal on the Periodic Table, a transition metal alkoxide will have from three to six alkoxide groups or a mixture of oxo and alkoxide groups. In one embodiment, an alkoxide group has from 2 to 4 carbon atoms, and includes, for example, ethoxide, propoxide, iso-propoxide, butoxide, iso-butoxide, tert-butoxide and fluoronated alkoxide. In one embodiment, a metal alkoxide for use in the present invention is zirconium tetra(tert-butoxide). In another embodiment, a metal alkoxide for use in the present invention is tantalum pentaethoxide. Suitable oxides for use in the present invention also include those described in U.S. Patent Publication No. 2009/0104474 and WO 09/052352, the entire contents of each of which are incorporated herein by reference. In one preferred embodiment, the oxide layer comprises a metal oxide. In another preferred embodiment, the metal oxide is formed from the precursor zirconium tetra(tert-butoxide).

The oxide is deposited onto the patterned base layer under conditions suitable to form an oxide layer on the patterned base layer. This may be achieved using any suitable technique known to one of ordinary skill in the art and includes, for example, vapor or immersion deposition and sol-gel processes. The step of forming a patterned oxide layer may include subjecting the oxide to pyrolysis, microwaving, complete hydrolysis or partial hydrolysis. In one embodiment, when heating conditions are employed, the oxide is heated to between about 50° C. and about the melting point of the polymer, e.g., not at or above the melting point of the polymer. In another embodiment, when heating conditions are employed, the oxide is heated to between about 50° C. and about the glass transition temperature of the polymer, e.g., not at or above the glass transition temperature of the polymer.

In a preferred embodiment, the oxide is deposited by vapor phase deposition of a metal alkoxide. In another preferred embodiment, the metal alkoxide is zirconium tetra(tert-butoxide).

The thickness of the patterned chemical layer is controlled by the deposition and heating times. Shorter exposure times for deposition (about 5 minutes) and heat (about 10 minutes) generally produce about a 1 nm layer (about 2 monolayers). The thickness of the layer can be determined by, for example, quartz crystal microgravimetry (QCM).

In an embodiment, the patterned chemical layer is about 0.1 to about 100 nm, 0.1 to about 70 nm, about 0.1 to about 50 nm, about 0.1 to about 30 nm, 0.1 to about 20 nm, about 0.1 to about 10 nm, is about 0.1 to about 10 nm, 0.1 to about 7 nm, about 0.1 to about 5 nm, about 0.1 to about 3 nm, 0.1 to about 2 nm, about 0.1 to about 1 nm, about 0.5 to about 2 nm, about 1 to about 2 nm, about 1 to about 1.5 nm, about 1.5 to about 2 nm, or about 0.1 nm, 0.5 nm, 1 nm, 1.1 nm, 1.2 nm, 1.3 nm, 1.4 nm, 1.5 nm, 1.6 nm, 1.7 nm, 1.8 nm, 1.9 nm, 2 nm, 2.1 nm, 2.2 nm, 2.3 nm, 2.4 nm, 2.5 nm, 2.6 nm, 2.7 nm, 2.8 nm, 2.9 nm, 3.0 nm, 3.1 nm, 3.2 nm, 3.3 nm, 3.4 nm, 3.5 nm, 3.6 nm, 3.7 nm, 3.8 nm, 3.9 nm, 4.0 nm, 4.1 nm, 4.2 nm, 4.3 nm, 4.4 nm, 4.5 nm, 4.6 nm, 4.7 nm, 4.8 nm, 4.9 nm, 5.0 nm, 5.1 nm, 5.2 nm, 5.3 nm, 5.4 nm, 5.5 nm, 5.6 nm, 5.7 nm, 5.8 nm, 5.9 nm, 6.0 nm, 6.1 nm, 6.2 nm, 6.3 nm, 6.4 nm, 6.5 nm, 6.6 nm, 6.7 nm, 6.8 nm, 6.9 nm, 7.0 nm, 7.1 nm, 7.2 nm, 7.3 nm, 7.4 nm, 7.5 nm, 7.6 nm, 7.7 nm, 7.8 nm, 7.9 nm, 8.0 nm, 8.1 nm, 8.2 nm, 8.3 nm, 8.4 nm, 8.5 nm, 8.6 nm, 8.7 nm, 8.8 nm, 8.9 nm, 9.0 nm, 9.1 nm, 9.2 nm, 9.3 nm, 9.4 nm, 9.5 nm, 3.6 nm, 9.7 nm, 9.8 nm, 9.9 nm, or about 10.0 nm in thickness. In another embodiment, the patterned chemical layer is 2 nm or less in thickness. In an embodiment, the patterned chemical layer is about 1 to about 1.5 nm in thickness. In an embodiment, the patterned chemical layer is about 10 to about 70 nm in thickness. In another embodiment, multiple layers of a semi-rigid or soft polymer are coated on the base layer so long as the polymer can still flex. It should be understood that a range between any two figures listed above is specifically contemplated to be encompassed within the metes and bounds of the present invention.

The patterned oxide layer can be about 1 to about 50, about 1 to about 45, about 1 to about 40, about 1 to about 35, about 1 to about 30, about 1 to about 25, about 1 to about 20, about 1 to about 15, about 1 to about 10, about 1 to about 5, about 2 to about 50, about 2 to about 45, about 2 to about 40, about 2 to about 35, about 2 to about 30, about 2 to about 25, about 2 to about 20, about 2 to about 15, about 2 to about 10, about 2 to about 5, about 5 to about 50, about 5 to about 45, about 5 to about 40, about 5 to about 35, about 5 to about 30, about 5 to about 25, about 5 to about 20, about 5 to about 15, about 5 to about 10, about 10 to about 50, about 10 to about 45, about 10 to about 40, about 10 to about 35, about 10 to about 30, about 10 to about 25, about 10 to about 20, about 10 to about 15, about 20 to about 50, about 25 to about 50, about 30 to about 50, about 35 to about 50, about 40 to about 50, or about 45 to about 50 monolayers thick. Ranges and values intermediate to the above recited ranges and values are also contemplated to be part of the invention. For example, 1-3 and 7-11 monolayer thicknesses are intended to be encompassed by the present invention.

In one embodiment, the patterned oxide layer is about 1 to about 10, about 1 to about 9, about 1 to about 8, about 1 to about 7, about 1 to about 6, about 1 to about 5, about 1 to about 4, about 1 to about 3, about 1 to about 2 monolayers thick. In one embodiment, the patterned oxide layer is more than about 2 monolayers thick. In another embodiment, the patterned oxide layer less than about 2 monolayers thick. In another embodiment, the patterned oxide layer about 1 monolayer thick.

For making a scaffold that further comprises a cell adhesive layer, a cell adhesive chemical compound is deposited onto the patterned oxide layer, to form a patterned cell adhesive layer. The cell adhesive chemical compound is any organic compound that is sufficiently reactive with the oxide layer, e.g., sufficiently reactive with a metal oxide or alkoxide, such as, for example, an organic compound comprising a phosphonic, carboxylic, sulfonic, phosphinic, phosphoric, sulfinic, or hydroxamic group. Any suitable method may be used to deposit the organic layer onto the patterned oxide layer. In one embodiment, the cell adhesive chemical compound is deposited onto the patterned oxide layer by a dipping method.

In one embodiment, the patterned oxide layer is contacted with a phosphonic acid to generate a patterned cell adhesive layer comprising a phosphonate. As used herein, the term "phosphonic acid" refers to a group, or compound that includes a group of formula —P(=O)(OH)2 attached to a carbon atom, As used herein, the term "phosphonate," refers to a group, or compound that includes a group of formula —P(=O)(OX)2 attached directly to a carbon atom where X is the metal from the patterned oxide layer.

In one embodiment, the acid used to treat the patterned oxide layer comprises any aliphatic or aromatic moiety and contains two acidic groups. In one embodiment the acidic groups are phosphonic acid groups (—P(=O)(OH)2). In another embodiment the acidic groups are carboxylic acid groups (—CO2H). In yet another embodiment the acidic groups are both phosphonic and carboxylic acid groups. In one embodiment the acid used to treat the patterned oxide layer comprises an alkyl chain. In one embodiment the alkyl chain is 4-18 carbons in length. In another embodiment the alkyl chain is optionally substituted with any aromatic or aliphatic moiety, e.g. an alkyl, aryl, alkenyl or alkynyl group. Non-limiting examples of phosphonic acids include α,ω-bisphosphonic acids. Non-limiting examples of carboxylic acids include α,ω-biscarboxylic acids. Nonlimiting examples of mixed phosphonic/carboxylic acids include α-carboxylic-ω-phosphonic acids. Non-limiting examples of mixed phosphonic/carboxylic acids include α-phosphonic-ω-carboxylic acids. In one embodiment, the bisphosphonic acid is an octadecylphosphonic acid (ODPA) derivative. In one embodiment, the phosponic acid is 1,4-butane-diphosphonic acid.

In some embodiments, a cell-avoidance layer is deposited on all or a portion of the patterned oxide layer. In one embodiment, a cell-avoidance layer may be deposited in a pattern that is complementary to a cell adhesive layer. A cell-avoidance layer is a layer that inhibits the adhesion of cells.

Exemplary compounds suitable for use as a cell-avoidance layer include, for example, compounds with terminal pegylated groups and those comprising an alkyl terminal group.

In certain embodiments, the scaffolds of the present invention further comprise living cells. Accordingly, in another embodiment, the present invention provides a method for making an artificial tissue comprising living cells attached to a tissue scaffold comprising contacting a tissue scaffold of the present invention with cells and culturing under conditions suitable for cell growth and/or differentiation. The type of cells is not limited, and includes, for example, fibro-blasts, endothelial cells, keratinocytes, osteoblasts, chondroblasts and chondrocytes, hepatocytes, macrophages, cardiac muscle cells, smooth muscle cells, skeletal muscle cells, tendon cells, ligament cells, neural cells, epithelial cells, and stem cells. Stem cells include embryonic stem cells, adult stem cells, and induced pluripotent stem cells. In one preferred embodiment, the cells are mesenchymal stem cells. In another preferred embodiment, the cells are human cells. Culture conditions for cell growth and/or differentiation are known to those of skill in the art.

As noted above, one embodiment of the invention encompasses a method for making a tissue scaffold comprising the steps of (1) generating a pattern on a base layer of protective photoresist compound stripes and unprotected base layer stripes using photolithography, to form a patterned base layer; and (2) depositing an oxide layer onto the unprotected stripes to form a patterned oxide layer. One embodiment further comprises contacting the patterned oxide layer of the substrate with cells; culturing the cells under conditions suitable for the production of extracellular matrix components; and removing the cells from the substrate to provide a tissue scaffold comprising an extracellular matrix component aligned on the stripes.

In certain embodiments, the scaffolds of the present invention further comprise an extracellular matrix component aligned in parallel with the pattern of stripes. Accordingly, in another embodiment, the present invention provides a method for making a tissue scaffold comprising generating a pattern of stripes on a base layer by photolithography to form a substrate having patterned base layer; depositing an oxide layer onto the patterned base layer to form a substrate having a patterned oxide layer; contacting the substrate having the patterned oxide layer with cells and culturing under conditions suitable for the production of extracellular matrix components; and removing the cells from the substrate to provide a tissue scaffold comprising an extracellular matrix component aligned in parallel with the stripes.

In yet another embodiment, the present invention provides a method for making a tissue scaffold comprising generating a pattern of stripes on a base layer by photolithography to form a substrate having patterned base layer; depositing an oxide layer onto the patterned base layer to form a substrate having a patterned oxide layer; contacting the patterned oxide layer with a non-biologic cell adhesive compound to generate a substrate having a patterned cell adhesive layer; contacting the substrate having the patterned cell adhesive layer with cells and culturing under conditions suitable for the production of extracellular matrix components; and removing the cells from the substrate to provide a tissue scaffold comprising an extracellular matrix component aligned in parallel with the stripes. Thus, one embodiment of the method further comprises contacting the patterned cell adhesive layer of the substrate with cells; culturing the cells under conditions suitable for the production of extracellular matrix components; and removing the cells from the substrate to provide a tissue scaffold comprising an extracellular matrix component aligned on the stripes.

In the two foregoing embodiments, the patterned substrates comprising cells may be made by the methods described hereinabove, and then cultured under conditions suitable for the production of extracellular matrix components. Extracellular matrix components include, for example, fibronectin and collagens. Such conditions are known to those of skill in the art. These conditions include culturing cells at sufficient density in the presence of growth factors or serum. The skilled artisan can optimize conditions for different cell types. Additives may be used to stimulate the production of certain proteins. For example, type I collagen production may be stimulated by adding ascorbic acid to the culture medium.

After production of extracellular matrix components, the cells may be removed from the substrate, i.e., the substrate is decellularized. Methods for decellularizing are known in the art and include, for example, methods to loosen cell attachments from the extracellular matrix followed by lysis of cell membranes and solubilization of intracellular components under conditions that maintain the integrity and activity of the matrix. For example, decellularization may be accomplished by treatment to remove calcium by chelation to loosen cell attachments, followed by incubation with non-ionic detergent in a hypotonic buffer at alkaline pH to lyse cell membranes and solubilize intracellular components.

The scaffolds comprising an extracellular matrix component may further comprise living cells attached to the matrix component. Accordingly, in another embodiment, the present invention provides a method for making an artificial tissue comprising living cells attached to a tissue scaffold comprising the step of contacting a tissue scaffold of the present invention with cells and culturing under conditions suitable for cell growth and/or differentiation. The type of cells is not limited, and includes, for example, fibroblasts, endothelial cells, keratinocytes, osteoblasts, chondroblasts and chondrocytes, hepatocytes, macrophages, cardiac muscle cells, smooth muscle cells, skeletal muscle cells, tendon cells, ligament cells, neural cells, epithelial cells, and stem cells. Stem cells include embryonic stem cells, adult stem cells, and induced pluripotent stem cells. In one preferred embodiment, the cells are mesenchymal stem cells. In another preferred embodiment, the cells are human cells. The cells need not be the same cells used to produce the extracellular matrix component on the substrate. The cells may be obtained from a subject to be treated with the artificial tissue generated on the substrate. Culture conditions for cell growth and/or differentiation are known to those of skill in the art.

For example, cells may be attached by placing the scaffold in culture with a cell suspension and allowing the cells to settle and adhere to the surface. Cells respond to the patterning in terms of adherence and in terms of assembling ECM proteins in the pattern on the scaffold. Cells also respond to the patterning in terms of maturation, growth and function. The cells on the scaffold may be cultured in an incubator under physiologic conditions (e.g., at 37° C.) until the cells form a two-dimensional (2D) tissue, the orientation of which is determined by the pattern provided on the tissue scaffold.

Any appropriate cell culture method may be used to establish the tissue on the tissue scaffold. The seeding density of the cells will vary depending on the cell size and cell type but can easily be determined by methods known in the art. In one embodiment, cells are seeded at a density of between about $1 \times 10^3$ to about $6 \times 10^5$ cells/cm$^2$, or at a density of about $1 \times 10^3$, about $2 \times 10^3$, about $3 \times 10^3$, about $4 \times 10^3$, about $5 \times 10^3$, about $6 \times 10^3$, about $7 \times 10^3$, about $8 \times 10^3$, about $9 \times 10^3$, about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $1 \times 10^5$, about $1.5 \times 10^5$, about $2 \times 10^5$, about $2.5 \times 10^5$, about $3 \times 10^5$, about $3.5 \times 10^5$, about $4 \times 10^5$, about $4.5 \times 10^5$, about $5 \times 10^5$, about $5.5 \times 10^5$, about $6 \times 10^5$, about $6.5 \times 10^5$, about $7 \times 10^5$, about $7.5 \times 10^5$, about $8 \times 10^5$, about $8.5 \times 10^5$, about $9 \times 10^5$, about $9.5 \times 10^5$, about $1 \times 10^6$, about $1.5 \times 10^6$, about $2 \times 10^6$, about $2.5 \times 10^6$, about $3 \times 10^6$, about $3.5 \times 10^6$, about $4 \times 10^6$, about $4.5 \times 10^6$, about $5 \times 10^6$, about $5.5 \times 10^6$, about $6 \times 10^6$, about $6.5 \times 10^6$, about $7 \times 10^6$, about $7.5 \times 10^6$, about $8 \times 10^6$, about $8.5 \times 10^6$, about $9 \times 10^6$, or about $9.5 \times 10^6$ cells/cm$^2$. Values and ranges intermediate to the above-recited values and ranges are also contemplated by the present invention.

In one embodiment of the invention, the patterned tissue scaffold is contacted with a plurality of cells and cultured such that a living tissue, e.g., a tissue having at least in part, in vivo biological activity, is produced. In one embodiment, a living tissue is removed from the tissue scaffold. In one embodiment the patterned tissue scaffold comprises a plurality of cells on the stripes, and can be organized into a tissue structure. The cells can comprise human cells. Further the cells can consist essentially of a member selected from the group consisting of fibroblasts, endothelial cells, keratinocytes, osteoblasts, chondroblasts, chondrocytes, hepatocytes, macrophages, cardiac muscle cells, smooth muscle cells, skeletal muscle cells, tendon cells, ligament cells, neural cells, epithelial cells, and stem cells.

II. Exemplary Uses of the Patterned Tissue Scaffolds of the Invention

The patterned tissue scaffolds of the invention (and/or a living tissue prepared on a tissue scaffold and removed from the scaffold) may be used in a broad range of applications, including, but not limited to, devices for use in tissue repair and support such as sutures, surgical and orthopedic screws, and surgical and orthopedic plates, natural coatings or components for synthetic implants, cosmetic implants and supports, repair or structural support for organs or tissues, substance delivery, bioengineering platforms, platforms for testing the effect of substances upon cells, cell culture, wound healing, neural regeneration and numerous other uses. In one embodiment, the living tissue is removed from the scaffold prior to use. In another embodiment, the living tissue is not removed from the scaffold prior to use.

The base layer of the patterned tissue scaffolds of the present invention may be tissue prepared on the tissue scaffolds of the invention or a medical device, such as an orthopedic screw or plate that comprises cells of the same tissue in which the devices will be used. Non-limiting examples of medical devices suitable for use in the present invention include, diagnostic implant devices, biosensors, stimulators, diabetic implants such as glucose monitoring devices, external fixation devices, external fixation implants, orthopedic trauma implants, implants for use in joint and spinal disorders/reconstruction such as plates, screws, rods, plugs, cages, scaffolds, artificial joints (e.g., hand, wrist, elbow, shoulder, spine, hip, knee, ankle), wires and the like, oncology related bone and soft tissue replacement devices, dental and oral/maxillofacial devices, cardiovascular implants such as stents, catheters, valves, rings, implantable defibrillators, and the like, contact lenses, ocular implants, keratoprostheses, dermatologic implants, cosmetic implants, implantable medication delivery pumps; general surgery devices and implants such as but not limited to drainage catheters, shunts, tapes, meshes, ropes, cables, wires, sutures, skin staples, burn sheets, and vascular patches; and temporary/non-permanent implants.

In addition, because the methods described herein are applicable to soft polymeric base layers, flexible membranes comprising a patterned tissue scaffold may be used to support or connect tissue or structures that have experienced injury, surgery, or deterioration. For example, a patterned tissue scaffold comprising a soft polymer may be used as a graft to connect and/or bind tissue and provide a platform for tissue regeneration, internally or externally. In such instances, the soft polymer may be biodegradable or non-biodegradable.

Another exemplary use of the patterned soft tissue scaffolds of the invention is as a barrier for the prevention of post-operative induced adhesion(s). For example, because adhesions are the result of disorganized ECM, the patterned tissue scaffolds of the invention may be used to organize ECM deposition and prevent the formation of adhesions.

Yet another exemplary use of the patterned tissue scaffolds of the invention is as templates for nerve growth. For example, the patterned tissue scaffolds may be used to culture neural cells in a pattern mimicking the in vivo environment such that suitable neural connections form rather than the unorganized array of neural cells that are produced without use of a patterned scaffold. The patterned scaffolds are prepared according to FIG. 16.

The components of the nervous system are categorized as belonging to either the peripheral nervous system (PNS) or the central nervous system (CNS). The basic anatomy of the nervous system at a cellular level is defined by the presence of neurons, specialized cells which are electrically excitable and serve to transmit information through electrical and chemical signaling. Signaling between neurons occurs via synapses, which are membrane-to-membrane junctions between neuron cells, or between neurons and other cell tissues, for example between efferent nerve fibers and muscle fibers at the neuromuscular junction.

Aside from neurons, the other primary cellular component of the nervous system is glial cells. Glial cells are non-neuronal cells which provide support for neurons in a variety of manners, including maintaining homeostasis, providing nutrients and oxygen, providing structural integrity to the neural network, providing and maintaining a myelin sheath, and to combat pathogens and remove dead neurons. It is also possible that glial cells may assist neurons to form synaptic connections with other neurons.

The CNS is the part of the nervous system that is comprised of the brain and the spinal cord. The PNS is the part of the nervous system that is comprised of nerves that are outside the CNS, in that the PNS excludes the brain and the spinal cord. The PNS is primarily comprised of ganglia, which are clusters of neurons found in the PNS. Ganglia in the PNS are comprised mainly of somata and dendritic structures which are interconnected to other ganglia to form a system known as a plexus. Ganglia primarily function to provide intermediate connections between different neurological structures in the body, including different structures in the PNS, and between the PNS and the CNS. There are three major groups of ganglia found among vertebrate animals, which include the dorsal root ganglia, the cranial nerve ganglia, and the autonomic ganglia.

Neurons are comprised of a number of different structure features. At a basic level, neurons are comprised of dendrites, a soma (cell body) containing the nucleus and other essential cellular machinery, an axon, a long thin nerve fiber that conducts electrical impulses away from the dendrites to the axon terminal, which is oriented to another neuron's dendrites or to a target cellular tissue. A major characteristic of neurons is the presence or absence of a myelin sheath along the axon of the neuron. Neurons may be either myelinated or unmyelinated, depending on the location of the neuron in the nervous system. Myelin is an electrically insulating, i.e. dielectric material primarily comprised of lipids, proteins, cholesterol and water, the precise compositions of each varying by its location in the nervous system. The myelin sheath serves to increase the speed at which electrical impulses are conducted along the axon. In the PNS, Schwann cells (glial cells) provide the myelin sheath, whereas in the CNS, oligodendrocytes provide the sheath.

A defining characteristic of neurons is that once neural progenitor cells have fully differentiated into neurons, the neurons do not undergo any further cellular division. Instead, new neurons arise via neural stem cell differentiation.

Accordingly, in one embodiment, this invention relates to scaffolds for nerve tissue regeneration. In another embodiment, this invention relates to methods for regenerating nerve tissue. In general, the present invention provides methods of tissue repair and regeneration comprising implanting the artificial tissues of the present invention in a subject in need of such tissue repair or regeneration. Another embodiment is directed to a method of tissue repair or regeneration comprising implanting a tissue scaffold of invention into tissue in need of repair or regeneration in a subject in need thereof.

In one embodiment, neural cells seeded onto the patterned polymer scaffold will grow in alignment with the pattern on the polymer.

In another embodiment, once the decellularized, cell-assembled, aligned ECM patterned polymer scaffolding has been created according to the methods disclosed herein, neural cells may be seeded onto the scaffolding. The neural cells will grow in alignment with the fibrillar matrix. Quantification of neurite expansion has shown enhanced alignment of neural cells when cultured on patterned/aligned ECM compared to an unpatterned matrix. By controlling the initial alignment of the cells that synthesize the ECM, and in effect the ECM alignment, the scaffolding can be rendered bioactive to more precisely control and regulate nerve tissue growth, differentiation, and regeneration.

The neural cells which are seeded on the scaffolding can be induced to connect or reconnect with other neural cells, or potentially other cellular targets, for example, but not limited to, muscle tissue at the NMJ. This has wide potential therapeutic application as a treatment for a number of neurodegenerative diseases as well as aging.

There are a large number of cell types that are of potential use as neural cells. Some non-limiting examples include stem cells, including but not limited to, omnipotent, pluripotent, and induced pluripotent stem cells, for example, embryonic stem cells and adult stem cells including, but not limited to, neural stem cells (NSCs), as well as oligopotent stem cells including, but not limited to, neural progenitor cells and neuroblasts. Co-culture with glial support cells is another possibility, including, but not limited to CNS macroglial cells, for example, astrocytes and astrocyte precursor cells, oligodendrocytes and oligodendrocyte precursor cells, and PNS macroglial cells, for example Schwann cells and Schwann precursor cells. Further possible cell types include already differentiated neurons and glial cells, neural crest cells, such as those that give rise to the PNS, including, but not limited to, the dorsal root ganglia, and neural tube cells, such as those that give rise to the CNS, including, but not limited to, the basal ganglia.

Furthermore, there are a number of commercially available suitable cell culture lines for use with the present invention. These include, but are not limited to, the PC12/PC12 Adh cell line, derived from pheochromocytoma of the rate adrenal medulla. Other appropriate cell lines include, but are not limited to, those derived from neuroblasts, including, but not limited to, Neuro-2a, N1E-115, NB41A3, B104-1-1, which are cell lines derived from mice neuroblasts, and SK-N-AS, IMR-32, SK-N-DZ, SK-N-FI, BE(2)-M17, BE(2)-C, which are cell lines derived from human neuroblasts. Further appropriate cell lines include, but are not limited to, those derived from Schwann cell lines, including immortalized Schwann cell lines, for example, but not limited to, SW10 (mouse), R3 and RSC96 (rat) neuronal Schwann cells. One having ordinary skill in the art will appreciate that these cell lines listed are merely exemplary and many numerous other potential cell lines are appropriate for use with the current invention.

In some embodiments, patterned tissue scaffolds contacted or seeded with living cells are combined with a drug such that the function of an implant or graft will improve. For example, antibiotics, anti-inflammatories, local anesthetics or combinations thereof, can be added to the cell-treated a patterned tissue scaffold to speed the healing process. Other compounds, molecules, elements, or ions such as growth factors, trophic factors, cytokines, steroids, metabolites, and other signaling molecules and hormones such as those involved in growth and differentiation, for example, but not limited to, signaling molecules involved in neural development and differentiation, such as those signaling molecules involved in the Notch signaling pathway, may be added to the scaffolding in order to promote, direct, alter, or repress axon alignment, outgrowth, and neural regeneration and cellular growth.

In one embodiment, the tissues of the present invention can be used to study functional differentiation of stem cells (e.g., pluripotent stem cells, multipotent stem cells, induced pluripotent stem cells, and progenitor cells of embryonic, fetal, neonatal, juvenile and adult origin). For example, the patterned tissue scaffolds of the invention are contacted with undifferentiated cells, e.g., stem cells, and differentiation is observed.

Patterned tissue scaffolds containing cells are also useful for measuring tissue activities or functions, investigating tissue developmental biology and disease pathology, as well as in drug discovery.

Accordingly, the present invention also provides methods for identifying a compound that modulates a tissue function. The methods include providing a tissue scaffold comprising a tissue produced according to the methods of the invention, contacting the tissue with a test compound; and measuring the effect of the test compound on a tissue function in the presence and absence of the test compound, wherein a modulation of the tissue function in the presence of the test compound as compared to the tissue function in the absence of the test compound indicates that the test compound modulates a tissue function, thereby identifying a compound that modulates a tissue function.

In another aspect, the present invention also provides methods for identifying a compound useful for treating or preventing a disease. The methods include providing a tissue scaffold comprising a tissue produced according to the methods of the invention, contacting a tissue with a test compound; and measuring the effect of the test compound on a tissue function in the presence and absence of the test compound, wherein a modulation of the tissue function in the presence of the test compound as compared to the tissue function in the absence of the test compound indicates that the test compound modulates a tissue function, thereby identifying a compound useful for treating or preventing a disease.

PRESENT EMBODIMENTS

One embodiment of the invention is directed to a tissue scaffold comprising a base layer and an oxide layer, where the base layer and the oxide layer comprise a pattern of oxide layer stripes on the base layer, and the tissue scaffold further comprises a plurality of neural cells on the stripes, where the neural cells are selected from the group consisting of neural stem cells, oligopotent stem cells, differentiated neurons, differentiated glial cells and neural crest cells. One embodiment of the tissue scaffold further comprises a non-biologic cell adhesive layer disposed on the oxide layer. Another embodiment further comprises an extracellular matrix component aligned on the stripes. In one embodiment of the tissue scaffold the base layer is selected from the group consisting of a semi-rigid polymeric surface and a soft polymeric surface. In another embodiment the base layer is selected from the group consisting of polyesters, polyamides, polylactones, polyacrylamides and polysiloxanes. In yet another embodiment the base layer is selected from the group consisting of silk and collagen. In still another embodiment the base layer is selected from the group consisting of nylon, polyethylene terephthalate, polycaprolactone fumarate, polyethylene glycol fumarate, and methylene bis acrylamide.

In one embodiment of the tissue scaffold the stripes are about 5 µm to 100 µm wide and spaced about 5 µm to 100 µm apart. In some embodiments the stripes are about 5 µm wide and spaced about 5 µm apart, or about 10 µm wide and spaced about 10 µm apart, or about 20 µm wide and spaced about 20 µm apart, or about 30 µm wide and spaced about 30 µm apart, or about 20 µm wide and spaced about 10 µm apart.

In one embodiment of the tissue scaffold the oxide is a metal oxide. In one embodiment the metal oxide is zirconium oxide.

In some embodiments of the tissue scaffold the cell adhesive layer comprises a phosphonate.

In some embodiments of the tissue scaffold the oligopotent stem cells are selected from the group consisting of neural progenitor cells and neuroblasts.

In some embodiments of the tissue scaffold the neural crest cells are selected from the group consisting of dorsal root ganglia cells, neural tube cells, and basal ganglia cells.

In some embodiments the tissue scaffold is co-cultured with glial support cells. In some embodiments the glial support cells are selected from the group consisting of CNS macroglial cells and PNS macroglial cells. In some embodiments the CNS macroglial cells are selected from the group consisting of astrocytes, astrocyte precursor cells, oligodendrocytes and oligodendrocyte precursor cells. In some embodiments the PNS macroglial cells are selected from the group consisting of Schwann cells and Schwann precursor cells.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a tissue with a test compound) is intended to include any form of interaction (e.g., direct or indirect interaction) of a test compound and a tissue. The term "contacting" includes incubating a compound and a tissue (e.g., adding the test compound to a tissue).

Test compounds, may be any agents including chemical agents (such as toxins), small molecules, pharmaceuticals, peptides, proteins (such as antibodies, cytokines, enzymes, and the like), and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound may be added to a tissue by any suitable means. For example, the test compound may be added drop-wise onto the surface of a tissue of the invention and allowed to diffuse into or otherwise enter the tissue, or it can be added to the nutrient medium and allowed to diffuse through the medium.

All references cited herein are incorporated herein in their entireties.

The following examples serve to further illustrate the present invention.

Example 1

Materials and Methods

Materials: p-Type, heavily boron-doped silicon terminated with a 1000 Å thermally grown oxide layer (Silicon Quest, Inc.), polyetheretherketone, nylon 6,6, and polyethylene terephthalate films of 0.05 mm thickness (Goodfellow, Corp.), glass cover slips (12 mm, No. 2; VWR) were obtained from commercial sources. The dimensions of the photolithographic patterns used were (width of stripe X space between stripes; all nominal dimensions are in µm):

10×10, 20×20, 10×20, 20×10, 20×30, 30×10, 30×30, 40×30, 50×30, 60×30, and 100×40. Some minor shadowing was observed with stripes≤20 µm. Hexanes, toluene, methanol, 2-propanol, hexamethyldisilazane (HMDS), formaldehyde, 4',6-diamidino-2-phenylindole (DAPI), and anti-vinculin antibodies (Sigma-Aldrich); zirconium tetra(tert-butoxide) (Strem Chemicals, Inc.); fluorescein-tagged secondary antibody, Dulbecco's modified eagle medium (DMEM) (Invitrogen); bone marrow derived human mesenchymal stem cells (hMSCs, PT-2501), serum containing "bullet" medium (PT-3001), trypsin/EDTA (CC-3232) (Lonza); nonyl phenoxypolyethoxylethanol (NP-40), sulfuric and hydrochloric acids (EMD Chemicals); 30% hydrogen peroxide (J. T. Baker); rhodamine phalloidin (Molecular Probes); 1,4-butanediphosphonic acid (Acros Organics); AZ-5214E photoresist and AZ-312 MIF developer (Capitol Scientific, Inc.); absolute ethyl alcohol (Pharmco-Aaper) were used as received. Photomasks were fabricated using a Heidelburg DWL 66 laser writer equipped with a 20 mm focal length writehead. NIH 3T3 mouse fibroblasts and bone marrow derived hMSCs were passaged bi-weekly and were stored at 37° C. until use.

Cleaning of Substrates: Silicon wafers were cut into 1 cm×1 cm coupons; coupons and glass cover slips were cleaned by sequential sonication in hexanes, toluene, and methanol for 15 min. The samples were next immersed in "piranha" solution ($H_2SO_4$: 30% $H_2O_2$, 3:1) for 15 min at 85° C. followed by sequential rinsing in deionized water and 2-propanol, and then dried under a stream of nitrogen. A second acid cleaning was done in "buzzard" solution (HCl: 30% $H_2O_2$, 1:1) at 85° C. for 15 min; the samples were rinsed sequentially with deionized water and 2-propanol, and then dried under a stream of nitrogen. The cleaned surfaces were stored in a desiccator until use. Polymer films were cut into 1 cm×1 cm coupons and were cleaned by sonication in ethanol for 15 min. The substrates were rinsed with 2-propanol, dried under a stream of nitrogen, and stored in a desiccator until use.

Photolithography: Neither specialized equipment nor a clean room are required. Cleaned polymer and silicon surfaces were rinsed sequentially with ethanol and 2-propanol, then dried under nitrogen and finally heated (95° C.) for 10 min, with the exception of nylon and PET, which were not heated to avoid glass transition. HMDS was spin cast onto the substrate surfaces (4000 rpm, 40 sec) followed by AZ-5214E photoresist (4000 rpm, 40 sec). Substrates were baked for 45 sec (95° C.), exposed to UV (365 nm, 4 W) through a photomask for 30 sec, and then developed in AZ-312 MIF for 30-34 sec. The substrates were rinsed vigorously in deionized water and examined by optical microscopy. All patterns were fabricated and analyzed at minimum in duplicate.

Vapor Phase Deposition of Zirconium tetra(tert-butoxide) (1), and Formation of the self-assembled monolayer of phosphonate (SAMP): Substrates patterned with photoresist were placed inside a deposition chamber equipped with two valves; one was connected to vacuum and the other to a bulb containing zirconium tetra(tert-butoxide) (1). The chamber was evacuated to $1\times10^{-3}$ torr for 10 min. Samples were exposed to vapor of 1 for 3 min with the chamber opened to vacuum. The bulb and chamber were sealed, and the chamber was warmed to 50° C. for silicon and 75° C. for polymers, giving a cross-linked, zirconium oxide base layer. The chamber was then cooled to room temperature. The chamber was back-filled with zero-grade nitrogen, and valves were closed to isolate the chamber prior to dismounting. The chamber was opened, and the substrates were soaked in an ethanol solution of 1,4-butanediphosphonic acid (0.25 mg/mL) for 24 hr. The preparation of the nanoscale-patterned surface is depicted schematically in FIGS. 1A and 1B. The substrates were then rinsed sequentially with ethanol and 2-propanol, dried under nitrogen, and then inspected by optical microscopy. This procedure removes the HMDS, the photoresist, and any $ZrO_2$ on the photoresist to leave a negative pattern in which the SAMP/$ZrO_2$ is directly attached to the substrate. The ability to make multiple, patterned substrates is limited only by the size of the photolithographic mask, the UV source, and the deposition chamber.

Surface Characterization: SAMP/$ZrO_2$ was analyzed by X-ray photoelectron spectroscopy (XPS), scanning electron microscopy (SEM), and energy dispersion spectroscopy (EDS). A VG scientific ESCALab Mk II equipped with a Mg Kα (1253.6 keV) anode source operating at 15 keV accelerating voltage and 20 mA and a VG scientific hemispherical sector analyzer (HAS) detector were used. A pass energy of 50 eV was used to collect survey (1000 to 0 eV) XPS data. Detailed XPS data were collected at a pass energy of 20 eV with a dwell time of 500 µs and a step size of 0.05 eV. Data analysis was carried out using CasaXPS software (Casa Software Ltd.). Spectra were calibrated against adventitious C 1s (at 284.5 eV). SEM analysis used a FEI Quanta 200 Environmental-SEM equipped with an Oxford INCA Synergy 450 energy-dispersive X-ray microanalysis system with an X-Max 80 large area analytical silicon drift detector (SDD) at an acceleration voltage of 5 keV. Atomic force microscopy (AFM) was used to determine the height on the patterns deposited on the substrate coupons (Digital Instruments Multimode AFM in tapping mode).

Pattern stability studies: Silicon and glass substrates were photolithographically patterned with 30×30 stripes of $ZrO_2$ as described above. The substrates were immersed in serum-containing medium (DMEM with 10% calf serum) for 18 days. Glass and Si substrates were removed on days 3, 6, 9, 12, and 18 and were rinsed gently with PBS. Optical microscopy determined if the $ZrO_2$ stripes remained intact, XPS analysis was used to identify elemental presence on the surface, and AFM investigated the surface morphology.

Cell alignment, toxicity, and long term studies: Cell adhesion studies for statistical analysis of cell aspect ratio and alignment were conducted using NIH 3T3 fibroblasts. SAMP-Patterned and control (unpatterned SAMP) samples were placed in individual wells of 24-well plates and were rinsed twice with phosphate buffered saline (PBS). NIH 3T3 fibroblasts were plated at 30,000 cells per well on the substrates in serum-free DMEM and were allowed to attach at 37° C. for 3 hr. The medium was changed to DMEM with 10% calf serum and the attached cells were allowed to spread for an additional 21 hr (24 hr total). Cells were fixed using 3.7% formaldehyde in PBS for 15 min, permeabilized with 0.5% NP-40 in PBS for 15 min at room temperature, and stained with rhodamine-phalloidin and DAPI for cell shape and orientation studies. Images were captured using a Nikon TE2000U microscope.

Cell toxicity was studied using 3T3 cells plated on silicon surfaces completely coated with a SAMP of 1,4-butanediphosphonic acid bonded onto $ZrO_2$ as described above. Cells were plated as described above in duplicate, and were allowed to proliferate for 3 days; after 24 hrs and 3 days they were stained and analyzed as above. Cells were counted and cell-spreading areas were measured using ImageJ, 10 image fields were used for the measurements and field dimen-sions were 853 µm×683 µm. Cell doubling time was calculated assuming constant growth rate.

Long-term (8 day) cell studies were performed on silicon and polymer patterned surfaces. 3T3 Cells were plated at 30,000 cells/well in serum-containing DMEM (10% calf serum). Bone marrow-derived MSCs were trypsinized with trypsin/EDTA and plated at 30,000 cells/well in serum containing "bullet" medium. The cells were incubated at 37° C. as the cells grew to confluence. Time points on silicon were taken at 24 hr, 3 days, and 8 days at which time the cells were stained for imaging as described above. Polymer time points were 24 hr and 3 days. Cells were plated on all surfaces in duplicate.

Data Analysis and Statistics: Cell conformity with SAMP/$ZrO_2$ patterns on $SiO_2$/Si surfaces was evaluated in fluorescent cell images by applying the Fourier transform using an ImageJ script (Oval Profile Plot script available at rsbweb.nih.gov/ij/index.html) (X. Fu, H. Wang, *Tissue Eng. Pt. A* 2012, 18, 631); images were rotated to center maximum intensity peaks at 90°. Data were plotted using Origin 8.5 (OriginLab Ltd.) as intensity of radial sum versus angle. Peak fitting was used to obtain full width at half maximum (FWHM) values for comparison. Data from 0° to 180° are presented, three pictures were analyzed in each case, and the FWHM for each peak was averaged.

Cell aspect ratio was calculated using ImageJ and was defined as the ratio of cell width to length; measurements were made after 24 hr on both experimental and control surfaces. Long membrane projections that were ≤5.3 µm wide were not included in the measurement of the overall length. The angle of cell orientation was also measured with respect to that of the pattern for the experimental surfaces (see FIG. 2A). An arbitrary horizontal axis was defined as the reference for the control surfaces; typically 5 fields were analyzed to measure 100 cells. The Shapiro-Wilk test was used to determine if data were normally distributed (n=100, α<0.05). The Kruskal-Wallis one-way analysis of variance was used to test for significant difference between all experimental groups and the control for both cell aspect ratio and angle of orientation (n=100, α<0.05). The Mann-Whitney U nonparametric statistical hypothesis test was used to test for significance in a pair-wise manner comparing the experimental groups, individually, to the control; the Bonferoni correction was used to adjust the significance level (n=100, α<0.0045). Origin 8.5 software was used to generate box plots.

Example 2

Preparation and Characterization of Surface-Modified Substrates

Figure 1A:
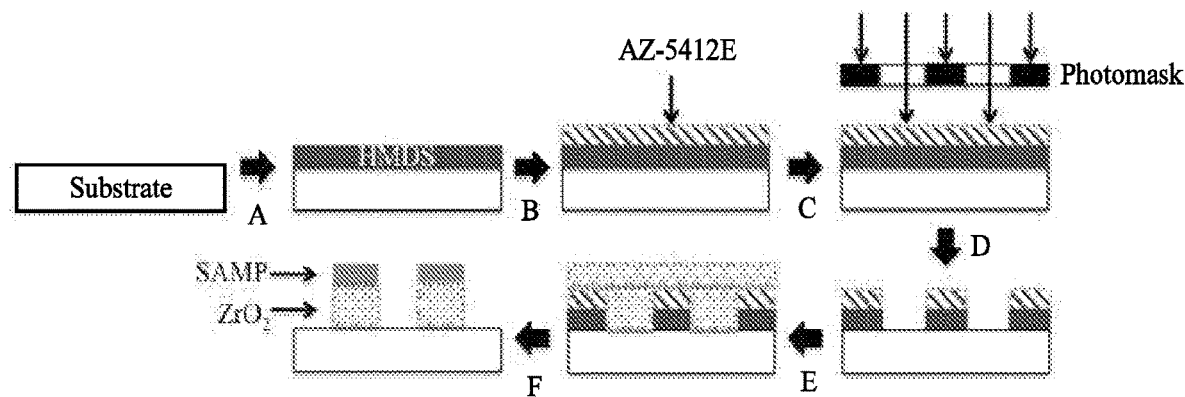
FIGS. 1A and 1B are schematics of the preparation of a nanoscale-patterned surface using a self-assembled monolayer of phosphonate (SAMP). 1A. (A) Spin-cast with hexamethyldisilazane (HMDS); (B) spin-cast AZ-5412E photoresist; (C) expose to UV through a photomask; (D) develop in AZ-312 MIF; (E) vapor deposition of zirconium tetra-t-butoxide (1), then heat to form adhesion layer; (F) assembly of the SAMP. 1B. The photolithographically patterned surface (E) is treated with vapor of 1 and then heated to give 2; reaction with phosphonic acid 3 gives SAMP/ZrO2/surface 4.
Figure 1B:
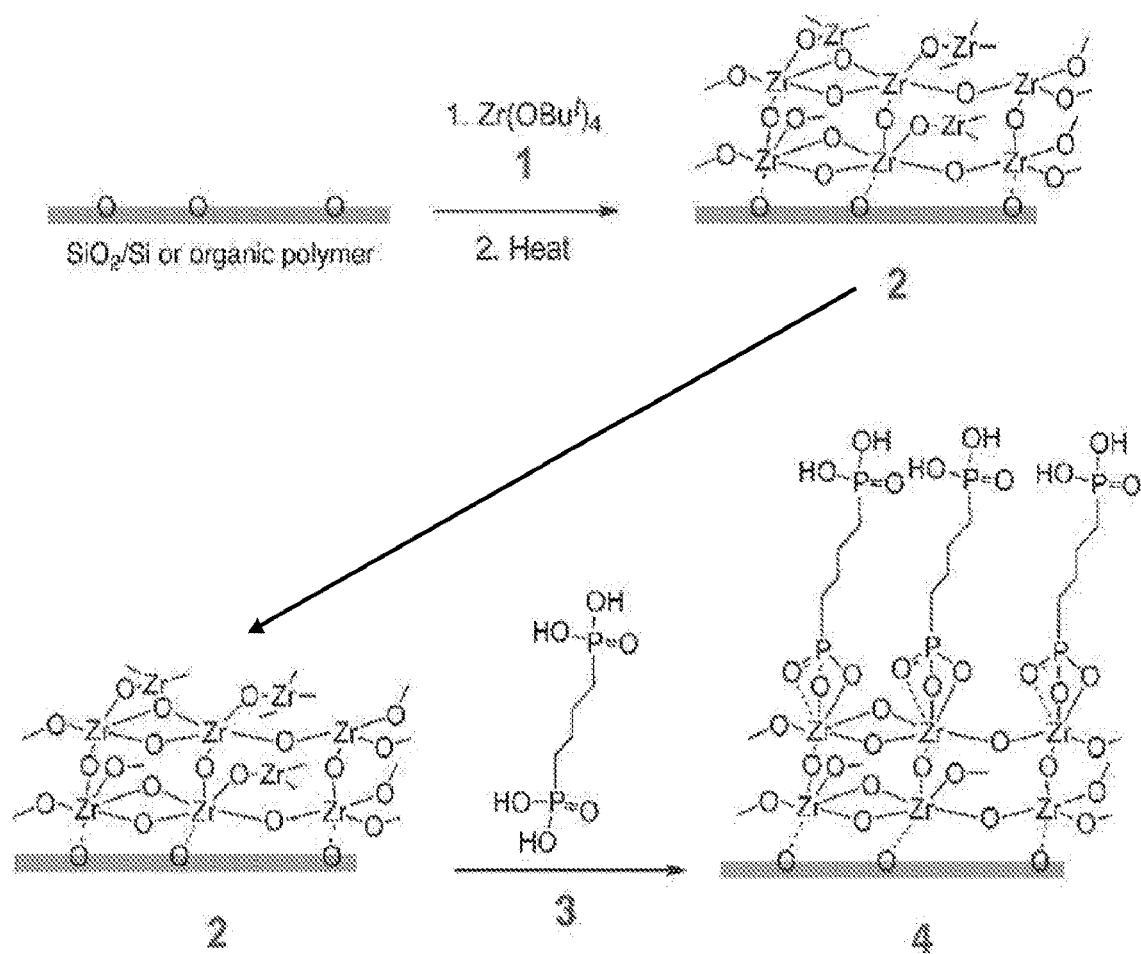

Materials surfaces were chemically modified as shown in FIG. 1A. Spin-casting of HMDS was followed by spin-casting AZ-5412E photoresist; the photoresist-coated material was exposed to UV light through a photomask of a negative of the desired striped pattern; the surface was developed in AZ-312 MIF to remove exposed photoresist; the substrate was exposed to vapor of zirconium tetra(tert-butoxide) (1) to yield the $ZrO_2$ layer when deposition was followed by mild thermolysis; the SAMP was then formed through immersion in an ethanol solution of 1,4-diphosphonobutane (this step also removed remaining photoresist exposing the underlying substrate). The synthesis of SAMP/$ZrO_2$/substrate (4) is outlined in FIG. 1B. Eleven striped patterns defined as the width of the SAMP/$ZrO_2$ stripe (in µm) X spacing between stripes (in µm), e.g., 20×30 were used.

Spectroscopic analysis was used to determine elemental composition and distribution of photolithographic patterns of SAMP/$ZrO_2$ on oxide-terminated Si ($SiO_2$/Si), PEEK, PET, and nylon 6,6. XPS analysis of a 30×30 striped pattern of the SAMP/$ZrO_2$/$SiO_2$/Si (4) showed peaks with binding energy (BE) $Zr(3d_{5/2})$=183.4 eV and BE P(2p)=134.3 eV, with relative integrated areas Zr:P≈1:1.5. Zirconium, P, C, and Si were mapped using SEM with EDS for a nominal 20×30 pattern on silicon, which showed conformity of Zr, P, and C with the pattern and with concomitantly reduced Si signal intensity (FIG. 2); the $P(K_\alpha)$ emission peak (2.013 keV) somewhat overlaps with the stronger $Zr(L_\alpha)$ peak (2.042 keV). Polymer surface characterization was performed on 60× SAMP-patterned surfaces using the same techniques.

AFM analysis of striped patterns of SAMP/$ZrO_2$/$SiO_2$/Si showed heights to be 10-70 nm; these nanoscale thick patterns should not affect physical properties of the substrate. AFM images of the SAMP/$ZrO_2$ pattern on PET showed an average height of 70 nm. Variations in height measured on any substrate surface are likely due to small changes in vapor-phase deposition conditions for 1.

Example 3

Stability of Patterns on Substrates

All surfaces maintained the $ZrO_2$ stripes intact for the duration of an 18 day study in which they were immersed in standard cell culture medium (10% calf serum in DMEM) at 37° C. Optical microscopy showed no evidence of stripe peeling or delamination. XPS analysis of coupons showed the persistence, but with signal attenuation, of the Zr 3d peak and with the appearance of an N 1s peak and higher binding energy shoulders on the C 1s peak These spectroscopic changes are attributed to serum protein adsorption onto the $ZrO_2$. Attenuation of the Zr 3d peak was somewhat more pronounced on the glass substrate, and it could not be detected after day 9. AFM analysis showed that the height of the patterned $ZrO_2$ stripe on Si (relative to that of underivatized regions) remained nearly constant following an initial increase in height within 9 days of immersion. For example, the initial pattern height of $ZrO_2$/$SiO_2$/Si was 12 nm; after immersion in culture medium this height increased to 20-25 nm and remained at this level for the duration of the study from day 3 to day 18. The $ZrO_2$/glass pattern height (before adding protein) was also 12 nm; after immersion it increased from 26 nm (day 3) to 50 nm (day 18). EDS analysis of the $ZrO_2$/$SiO_2$/Si pattern at day 3 showed, in addition to the striped pattern for Zr (as in FIG. 2 above), that nitrogen-containing material covered the entire surface.

Example 4

Cell Attachment, Spreading, and Orientation on Patterned Substrates

NIH3T3 fibroblasts were plated on SAMP/$ZrO_2$-patterned or unpatterned silicon surfaces and allowed to attach and spread for 3 hrs. Medium was replaced with DMEM/10% serum and, at 24 hr, cells were fixed and stained to visualize cell shapes and alignment (FIGS. 3A-3D). The cells attached preferentially to the SAMP/$ZrO_2$ patterns and nuclei were located almost entirely on the SAMP/$ZrO_2$ stripes. On closely spaced patterns (separated by 10 µm) cells were able to cross unpatterned areas and spread along adjacent SAMP/$ZrO_2$ stripes.

Figure 4:
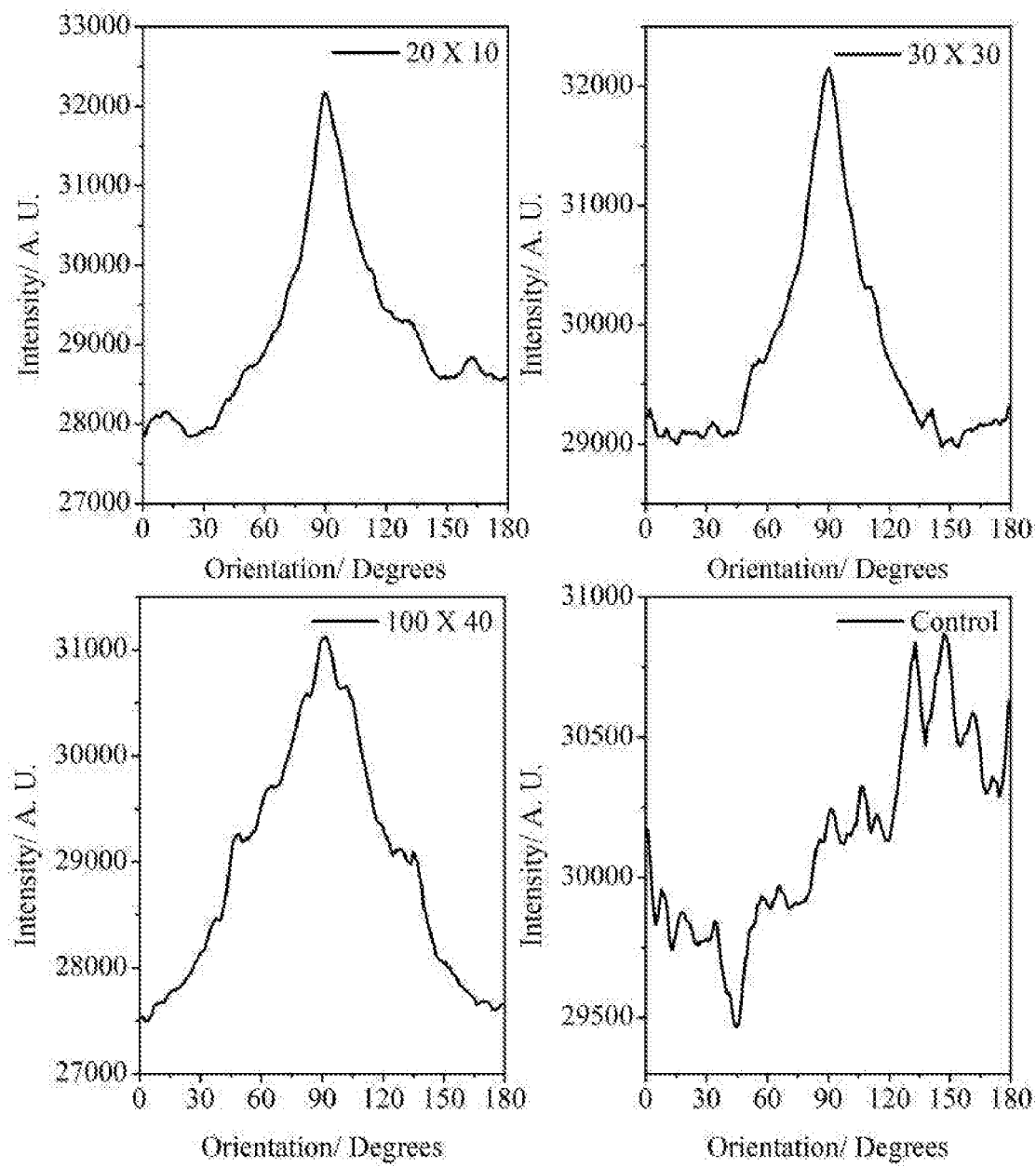
FIG. 4 illustrates intensities of the radial sums as a function of angle, which represents cell conformity with the SAMP/ZrO2/SiO2/Si pattern. These plots correspond to the images in FIGS. 3A-D. Full-width at half-maximum value (FWHM) for 20×10, 32°; 30×30, 29°; 100×40, 49°; FWHM for the control is not applicable. The peaks narrow as the dimensions decrease, indicating greater conformity of the cell to the pattern.

Fluorescent images of fixed and stained cells recorded 24 hr after seeding on SAMP/$ZrO_2$/$SiO_2$/Si patterned surfaces were used to determine the extent to which the cells conformed to the underlying pattern. Results of fast Fourier transformation (FFT) (X. Fu et al., *Tissue Eng. Pt. A* 2012, 18, 631) analysis of cell images (shown in FIG. 3A-3D) are plotted in FIG. 4. Plots show the intensity of fluorescence signal per pixel (but not cell alignment) vs. angle of orientation with regard to a defined axis. The full-width at half-maximum values (FWHM) of these distributions in degrees of rotation with regard to this axis provide a qualitative measure of cell conformity to the SAMP/$ZrO_2$ pattern: Lower FWHM values indicate better conformity to the pattern. Averages of three images gave FWHM values ranging from 27° for the 20×30 pattern to 49° for the 100×40 pattern.

Figure 2A:
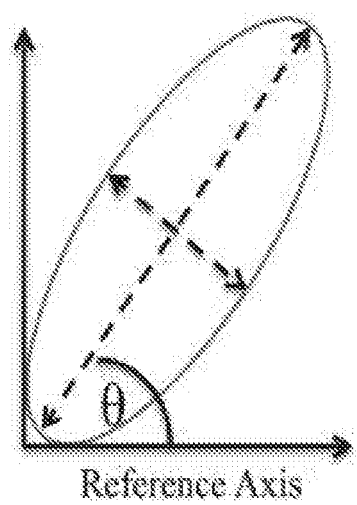
FIGS. 2A, 2B and 2C depict box plots for cell aspect ratio defined according to (A) and measured for (B) and angle of orientation (C). Plots represent the distribution of all measurements (n=100) for cell aspect ratio and angle of orientation. The boxes span 25-75 percentiles for the distributions; the whiskers span the 5-95 percentiles. The square is at the average value, and the horizontal line is at the median. The asterisk (*) denotes no statistical difference compared to the control.
Figure 2B:
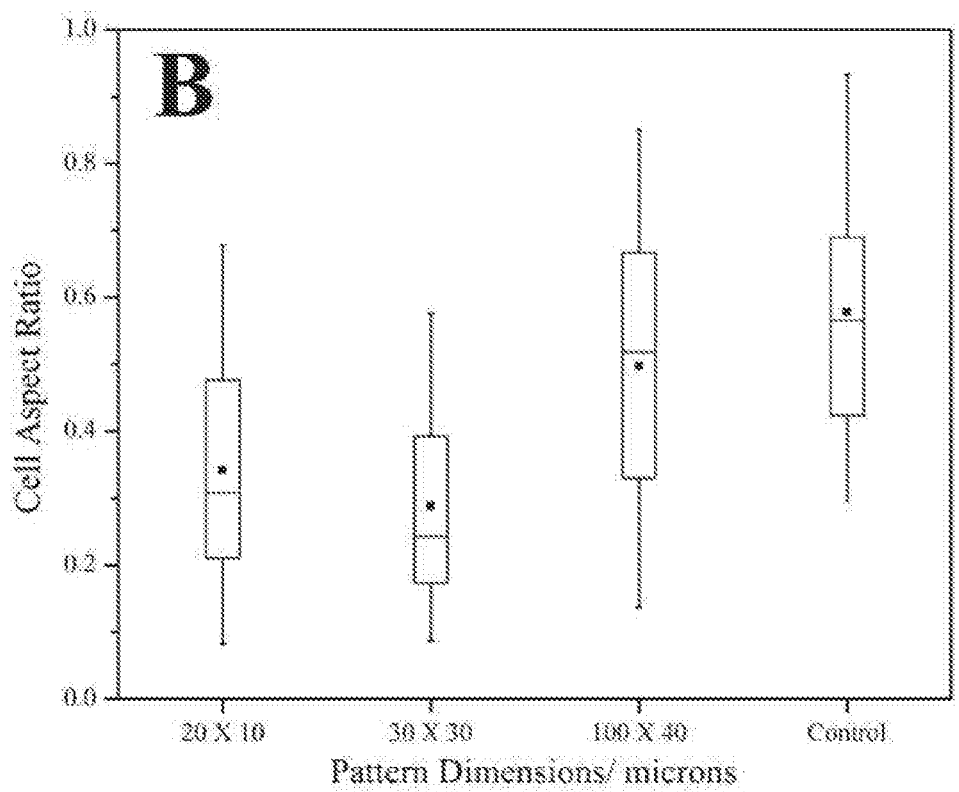
Figure 2C:
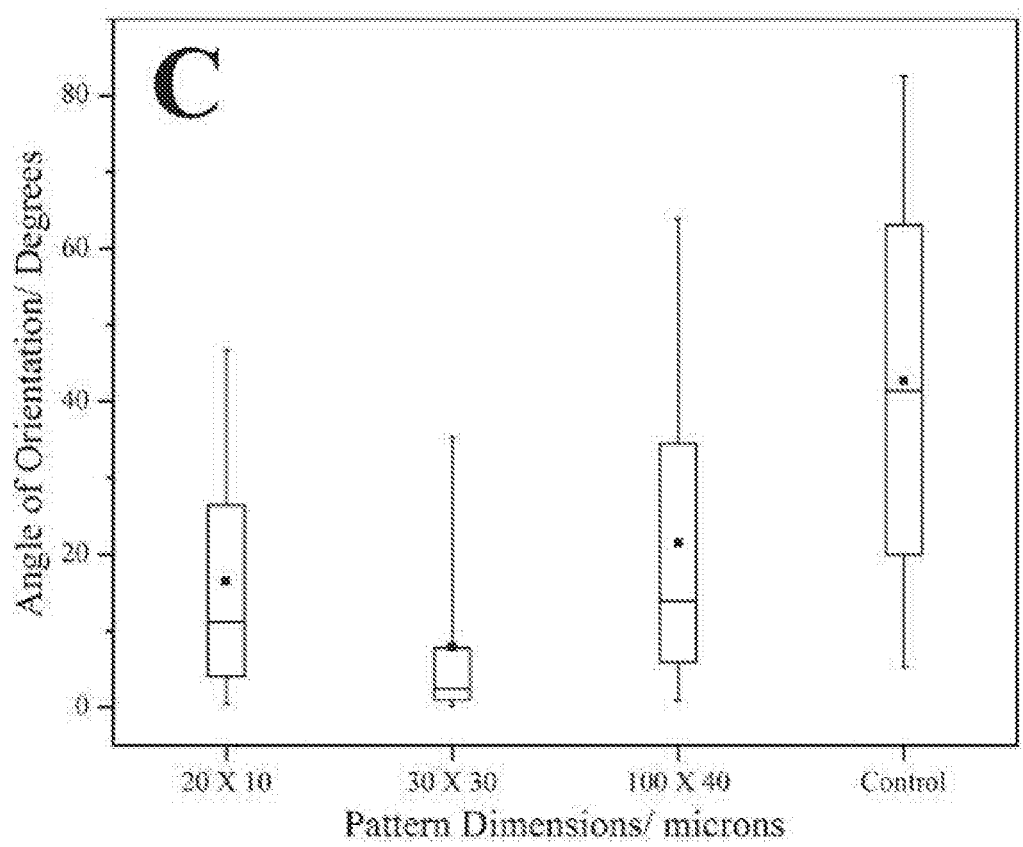
Figures 3A, 3B, 3C, 3D:
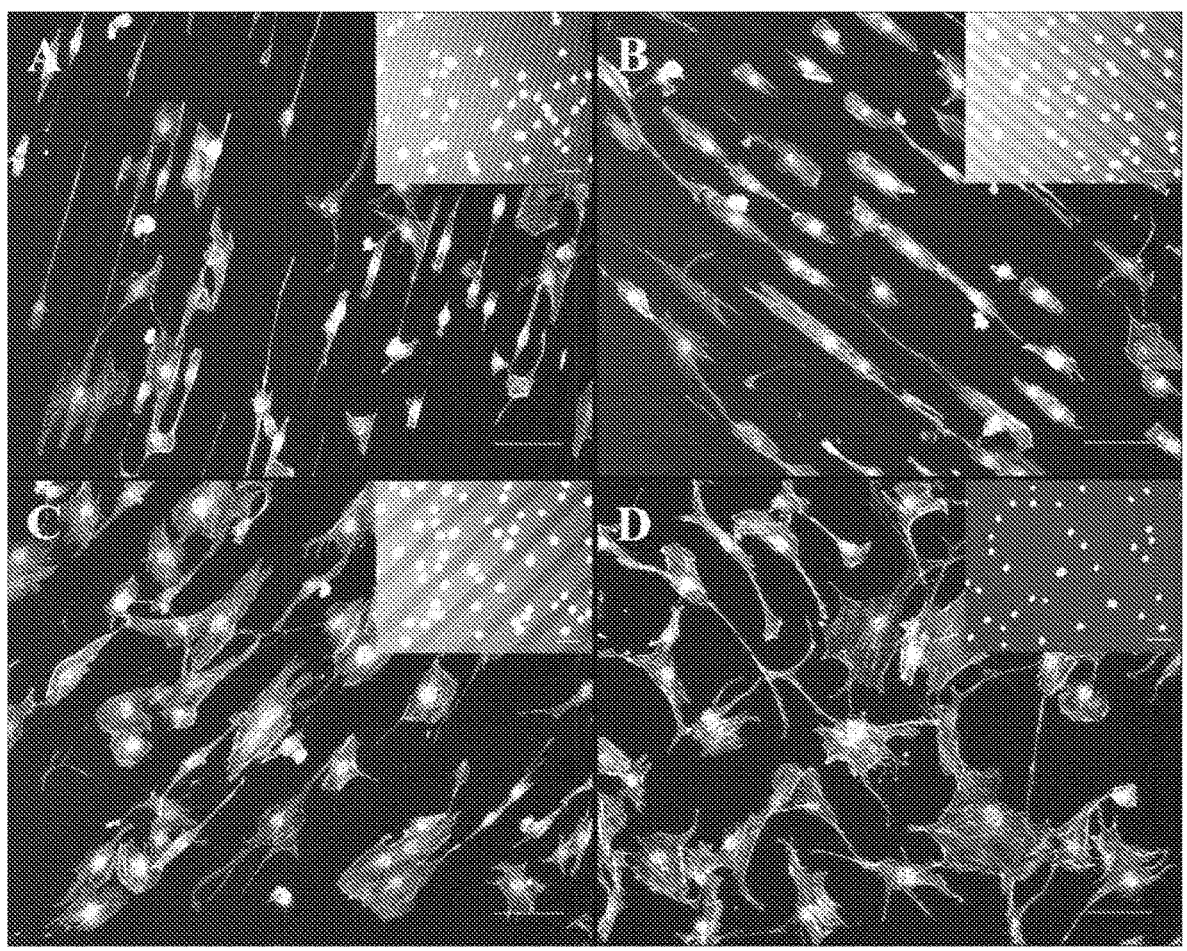
FIGS. 3A, 3B, 3C and 3D show NIH 3T3 cells spread on SAMP/ZrO2/SiO2/Si after 24 hr: (A) 20×10, (B) 30×30, (C) 100×40, (D) control. Scale bars=100 Actin filaments and nuclei are shown. Insets show conformity of cell attachment with the SAMP/$ZrO_2$ patterns (the lighter stripes).

A complementary analysis was done of cell aspect ratio (the ratio of cell width to length; an aspect ratio of 1.0 means the cell is perfectly round) and orientation of the cell long axis with regard to the pattern (FIG. 2A-2C). The "box-plots" represent the distribution of cell aspect ratio measurements (FIG. 2B). Analysis of variance for cell aspect ratio for all groups (patterns and control) found statistical difference ($p<0.001$) of at least one group to the others, and pair-wise analysis found all groups to be different from the control ($p<0.0001$), except the 100×40 pattern ($p=0.0184$). As shown in FIG. 2B, cells are more elongated on the narrower 20×10 and 30×30 patterns compared to unpatterned or 100×40 patterns. The distributions calculated for the 100×40 pattern (with the largest SAMP/$ZrO_2$ width studied) and the control substantially overlap. These results indicate that all of the SAMP/$ZrO_2$ pattern dimensions, with the exception of the 100×40 pattern, can influence cell shape to be statistically more elongated compared to an unpatterned control surface.

Cell alignment with the pattern direction was determined by measuring the angles of cellular long axes relative to the patterns. Analysis of variance found a statistical difference among the individual groups ($p<0.001$, $\alpha<0.05$), and pairwise comparison tests found statistical differences between each of the patterned surfaces compared to the control ($p<0.0001$, $\alpha<0.0045$) (FIG. 2C). In other words, all of these SAMP/$ZrO_2$ stripe dimensions can influence the direction of the cellular long axis in such a way that attached cells are oriented in the pattern direction compared to cells on an unpatterned surface. The 100×40 pattern can cause alignment of cells in the direction of the pattern but does not cause the cells to become more elongated than does an unpatterned surface. The 20×20 and 30×30 dimensions had the narrowest distributions for cell long axis orientation and pattern correspondence.

Example 5

Cell Proliferation on Patterned Substrates

After one day in culture SAMP/$ZrO_2$-treated substrates had 34±6 cells. Cell numbers increased on these surfaces over the next 3 days, to 134±32 cells; this corresponds to doubling times of 1.0 day. This is typical of cell growth on standard culture materials. Cell-spreading areas followed the same trend: after 1 day (3017±1830 $\mu m^2$), and at the end of the 3-day study (2912±1643 $\mu m^2$) for SAMP/$ZrO_2$-treated substrates. These data show that SAMP/$ZrO_2$-modified surfaces are not cytotoxic.

Example 6

Alignment of Cells on Patterned Substrates

Alignment of 3T3 Fibroblasts

Figures 5A, 5B, 5C, 5D, 5E, 5F, 5G, 5H, 5I:
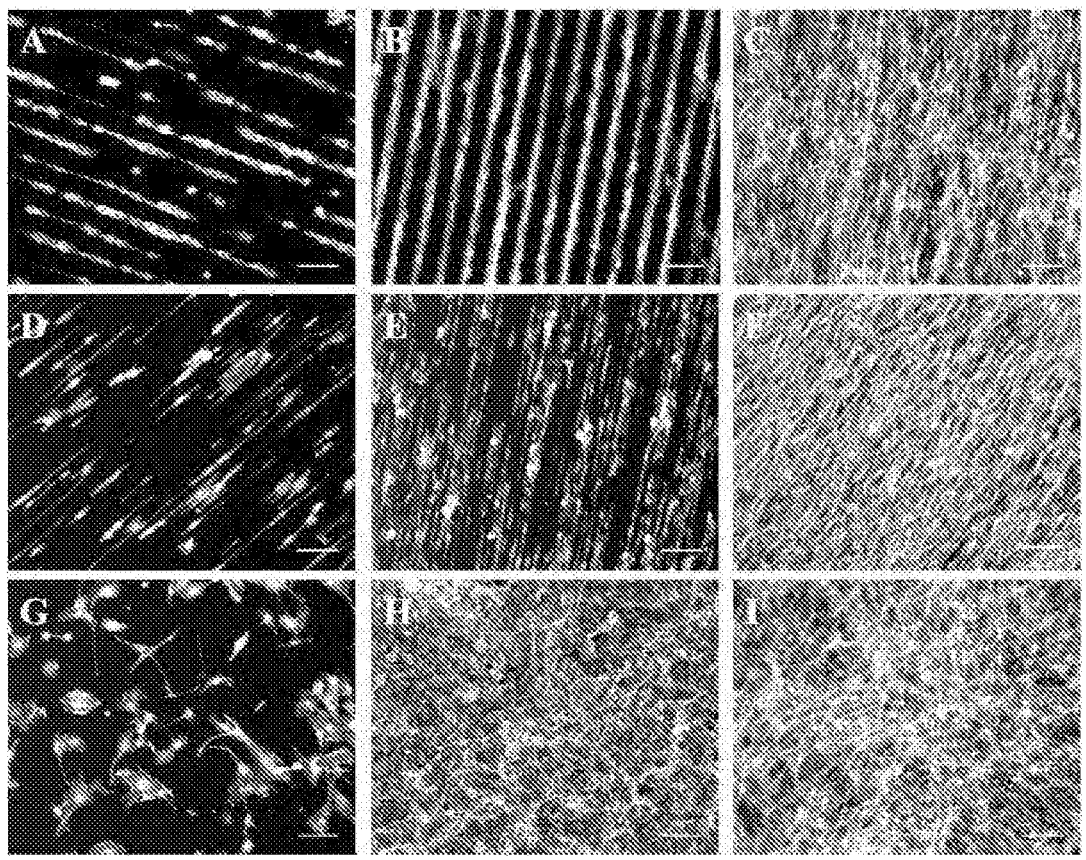
FIGS. 5A, 5B, 5C, 5D, 5E, 5F, 5G, 5H and 5I show 3T3 fibroblasts on 30×30 (top), 10×10 (middle) SAMP/ZrO2/SiO2/Si patterned surfaces and unpatterned control surfaces (bottom) after 24 hours, three days, and eight days. Images A, D and G after 24 hr; B, E, and H after 3 days; C, F, and I after eight days. As shown, 3T3 cells grow to confluence but remain in line with the chemical pattern. Images show actin stain; scale bar=100 μm; patterned directions in A-F are not identical with regard to the page.

The alignment of 3T3 fibroblasts on the foregoing patterns was maintained over 8 days; the cells grew to confluence and covered the entire 1 cm×1 cm silicon coupon. In this study 3T3 cells were plated on 10×10 and 30×30 stripes and on unpatterned control surfaces; time points were taken after 24 hr, 3 days, and 8 days with immunostaining of actin (FIG. 5A-5I). At 24 hr, 3T3 cells were aligned on the 30×30 stripes, and were oriented in the direction of the 10×10 pattern in which a single stripe is too narrow to entirely contain a cell (FIG. 5A, D). After 3 days, the cells on 30×30 and 10×10 surfaces had proliferated to cover most of the SAMP/$ZrO_2$ stripes and were oriented in the pattern direction (FIG. 5B, E). Cells on the control surface had grown to confluence and were randomly oriented (FIG. 5G, H). By day 8, cells had grown to confluence on both 10×10 and 30×30 SAMP/$ZrO_2$-patterned surfaces and remained aligned in the direction of the underlying chemical pattern (FIG. 5C, F). Since no physical channeling or barriers were used and the SAMP/$ZrO_2$ pattern is very thin (no more than 70 nm high), cells are free to spread across the less adhesive stripes and can form a confluent layer.

Alignment of MSCs

Figures 6A, 6B, 6C, 6D, 6E, 6F:
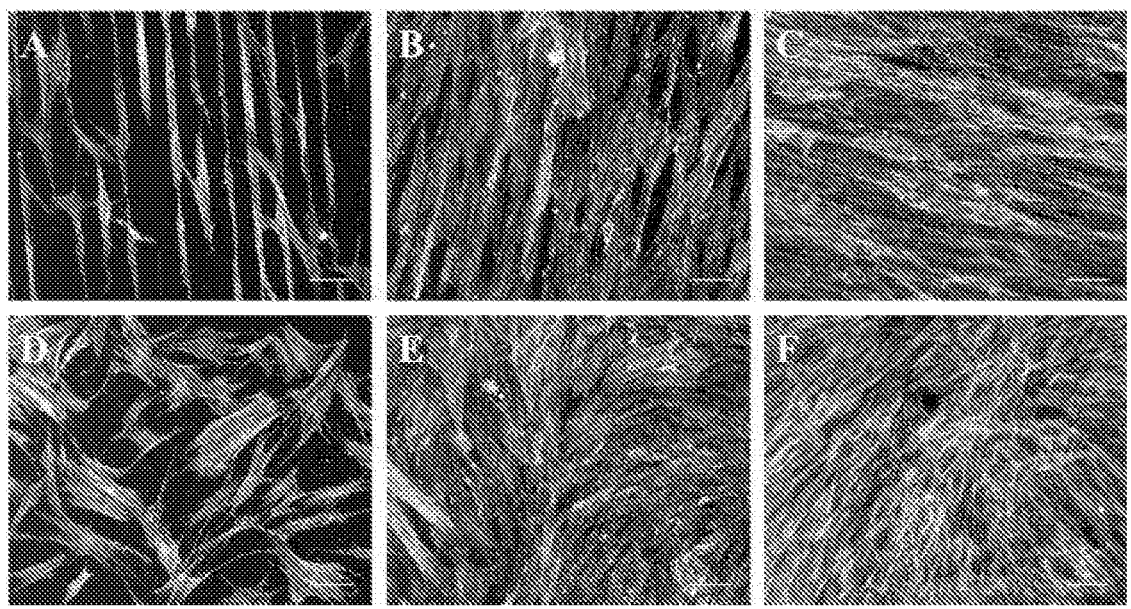
FIGS. 6A, 6B, 6C, 6D, 6E and 6F show bone marrow derived hMSCs on 30×30 SAMP/ZrO2/SiO2/Si patterned surfaces (A-C) and control, unpatterned surfaces (D-F). Images A and D after 24 hr, B and E after 3 days, and C and F after 8 days. As shown, hMSCs align with the chemical pattern and remain in alignment as they grow to confluence over 8 days; no directionality was observed for the unpatterned, control surfaces. Scale bars=100 μm; patterned directions in A-C are not identical with regard to the page.

Similar experiments were performed with human bone marrow-derived MSCs on a representative 30×30 pattern or on an unpatterned surface as a control on $SiO_2$/Si. Alignment of MSCs was examined by immunofluorescence staining of the actin cytoskeleton after 1, 3, and 8 days (FIG. 6A-6F). After 24 hr the MSCs were aligned with and spread on the pattern surface with some cells spread across two stripes. Stem cells on the unpatterned control were well spread but randomly oriented (compare FIGS. 6A and 6D). As cells grew to confluence, they remained aligned with the pattern (FIG. 6B, C) in contrast to cells on the control surface which were randomly spread (FIG. 6E, F). Therefore, MSCs and fibroblasts displayed a similar response to a 30×30 patterned substrate.

Example 7

Patterning on Polyester, Polyamide, and PEEK

Figures 7A, 7B, 7C, 7D, 7E, 7F, 7G, 7H, 7I:
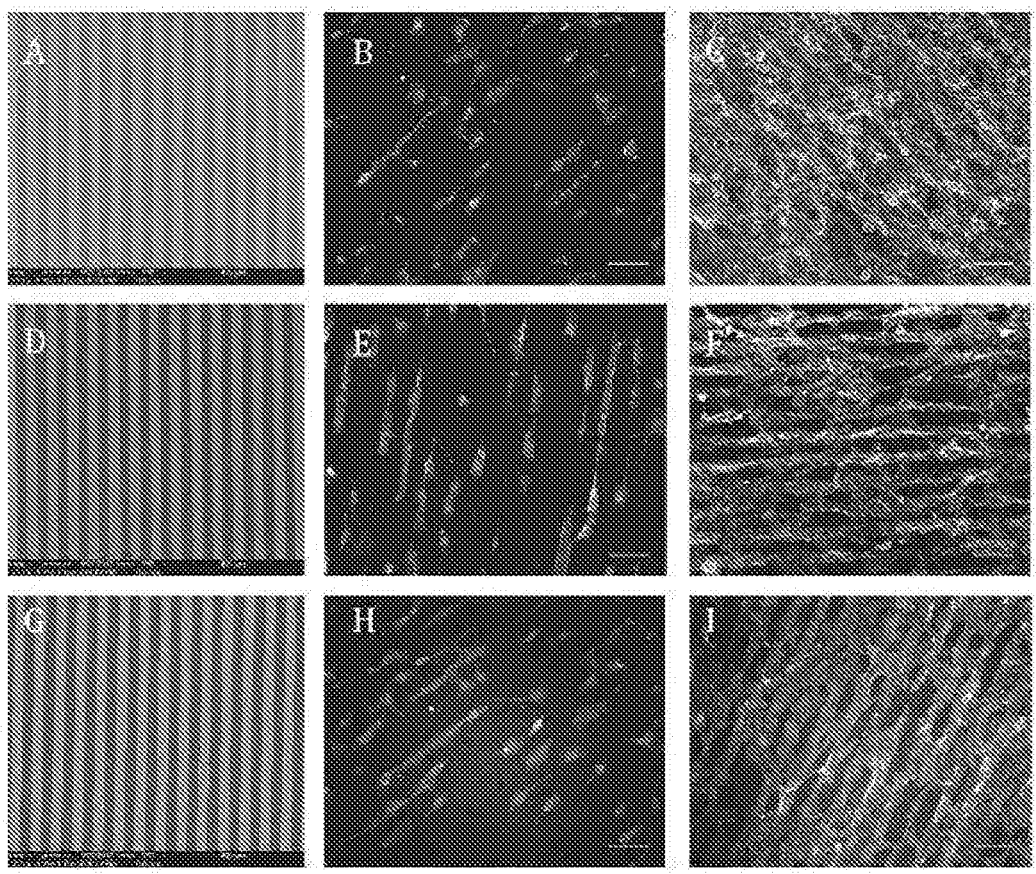
FIGS. 7A, 7B, 7C, 7D, 7E, 7F, 7G, 7H and 7I show SEM images (Magnification=200×) of 30×30 SAMP/ZrO2 on Nylon (A), polyethylene terephthalate (PET; D), polyetheretherketone (PEEK; G). As shown, the pattern is uniform across the polymer surface, with well-defined edges. 3T3 Fibroblasts on patterned Nylon (B), PET (E), and PEEK (H)

Photolithographic patterning was extended to polymers that are representative of three classes of biomaterials, polyesters (PET), polyamides (nylon), and polyetheretherketone (PEEK), which may be used for biomedical purposes as implantable devices or tissue scaffolds. The same vapor phase synthetic procedure used for surface patterning Si described hereinabove was applicable to these polymer materials (FIG. 7A, D, G). NIH 3T3 fibroblasts plated on 30×30 patterned SAMP/$ZrO_2$ polymer surfaces adhered to and aligned with the pattern with conformity comparable to that which was found for these dimensions on $SiO_2$/Si (FIGS. 7A-7I).

Example 8

Production of Aligned ECM on Polymer Substrate

The polyethylene terephthalate (PET) sheet with thickness of 0.05 mm was used as received (Goodfellow Corp., Oakdale, Pa.). The sheet was cut into ~0.5 cm×0.5 cm square pieces with a notch in the upper right corner to identify the top side of the PET film. The cut sheets were cleaned by sonication in isopropanol for 15 minutes, dried in a stream of nitrogen gas and warmed for 10 minutes before spin-coating at 3000 rpm with diazonaphthoquinone sulfonic ester positive photoresist (AZ5214-E). The resist was cured for 45 seconds and exposed to UV light through a photo-lithographic mask. Finally, the film was developed in tetram-ethyl-ammonium hydroxide solution (AZ312 MIF) to dissolve away the photoresist from the UV-exposed regions to provide 10×10, 30×30 and 60×30 patterns PET films micro-patterned with photoresist were placed in a glass chamber with inlets for vacuum and vapors of zirconium tetra(tert-butoxide), $Zr(OBu^t)_4$ (Sigma-Aldrich). The vacuum inlet was opened to evacuate the chamber to $10^{-3}$ torr. Both the inlets were opened for 5 minutes for vapor deposition under vacuum flow followed by closing the vacuum inlet for 5 minutes to allow deposition without external evacuation. The samples were heated to 47 deg C. using a heating tape to allow formation of surface-bound metal oxide $ZrO_2$ layer. The heating tape was removed and the chamber was cooled to room temperature. The PET films were then immersed promptly in 1 mM solution of 1,4-butane diphosphonic acid (Acros Organic) solution in ethanol for 17 hours. The patterned films were sonicated for 3 minutes, rinsed with isopropanol and dried in a stream of nitrogen gas.

NIH3T3 (ATCC) cells were cultured in DMEM supplemented with 10% bovine calf serum. The cells were maintained at 37° C. in a humidified incubator containing 5% carbon dioxide. NIH3T3s were trypsinized every 3-4 days and were re-plated for the next passage.

Before seeding, the PET sheet was disinfected using 70% ethanol for 20 minutes, washed three times with sterile phosphate buffered saline (PBS) and immersed in 1 ml DMEM in a 24-well plate. NIH3T3s were lifted from the culture plate using trypsin and suspended in media supplemented with 10% serum to inactivate the trypsin. The cell suspension was centrifuged and the cell pellet was re-suspended in media without added serum. The cells were counted using a hemocytometer and the PET sheet was seeded with 50,000 NIH3T3s. The cells were allowed to adhere to PET substrate in absence of serum proteins for 4 hours at 37° C. After adhesion, NIH3T3s were cultured in media with 10% serum and the media was refreshed on day 3, 6 and 8. The media was supplemented with 50 µg/ml ascorbic acid on day 6 and 8 to augment collagen type I synthesis. The phase contrast images of NIH3T3 cells growing on PET were taken using a Nikon Eclipse TS100 microscope and a Cooke SensiCam QE High Performance camera. Cell alignment on the patterned PET is depicted in FIG. 8. Fibronectin immunostaining and fast Fourier transformation analysis confirmed that cells and fibronectin aligned with the pattern. Fibronectin alignment and quantification of alignment of cells are shown in FIG. 9. As shown in FIG. 10, fibronectin alignment correlated with the pattern dimension, with decreasing conformity as the patterned stripes become wider. As shown in FIG. 11, collagen type I immunostaining and fast Fourier transformation analysis demonstrated that collagen also aligned with the patterns, demonstrating that collagen alignment can be controlled by a chemical pattern on the substrate.

The PET substrate with adhered cells was decellularized by treatment to remove calcium by chelation to loosen cell attachments followed by incubation with non-ionic detergent in a hypotonic buffer at alkaline pH to lyse cell membranes and solubilize intracellular components (Mao and Schwarzbauer (2005) *Matrix Bio.* 6:389-99). The treatment leaves extracellular matrix aligned with the pattern. FIG. 12 shows extracellular matrix on patterned PET surfaces before and after decellularization, fibronectin (FN) alignment and collagen type I (Col-I) alignment after decellularization, and a scanning electron micrograph (SEM) of the entire matrix. As shown in FIG. 12, the alignment of the matrix fibrils is maintained after decellularization. The histogram and graph show that angular alignment of collagen on the pattern is good (a relatively narrow angular distribution), but that there is essentially no directionality of collagen on the unpatterned surface (the very broad "peak" on the lower portion of the graph).

Primed PC12 cells (surrogates for neurons) were seeded on the decellularized matrix and cultured in differentiating media for 72 hours. As shown in FIG. 13, neurites from plated PC12 cells were aligned with the pattern, while there was no alignment on the unpatterned control.

Example 9

Patterning of $ZrO_2$ and $ZrO_2$/SAMP

Striped patterns of 30 µm in width spaced by 30 µm (30×30) were prepared on nylon, PET and PEEK treated with $ZrO_2$ with or without further treatment with bisphosphonate SAMP as described in the previous examples. For substrates treated with $ZrO_2$ alone, the surface was exposed to vapor of the zirconium alkoxide precursor of $ZrO_2$ for 5 minutes ($ZrO_2$ 5 min) or 10 minutes ($ZrO_2$ 10 min) before heating to make the oxide. The longer the time of initial exposure, the thicker the layer of oxide that formed. The $ZrO_2$ 5 min patterned substrate was used for further treatment with bisphosphonate SAMP. NIH3T3 fibroblasts (30,000 cells/well) were plated on the treated substrates and imaged after one day (FIG. 14) and 3 days (FIG. 15). As shown in FIGS. 14 and 15, there was significant cell alignment using $ZrO_2$ alone and very good cell alignment on SAMP-treated substrates.

Example 10

Formation of Decellularized, Cell-Assembled, Aligned ECM Patterned Polymer Scaffolding Volatile zirconium tetra(tert-butoxide) was condensed from the vapor phase onto a pat-terned substrate; it was then heated to generate cross-linked $ZrO_2$ that was bound to the polymer surface through coordination of its ester oxygen groups to the metal centers, which was substan-tiated by angle-dependent XPS analysis of the interface. Then, the substrate was dipped into a solution of the phosphonic acid to form the polymer-attached $ZrO_2$/SAMP, which enjoys a long shelf life at ambient temperature (see FIG. 16). In this way patterns of 10 µm wide stripes of $ZrO_2$/SAMP and 10 µm wide gaps (10 µm×10 µm pattern) were prepared on the poly(ethylene terephthalate) (PET) of Example 8, a polymer that is used in vascular graft biomaterials and is replete with ester carbonyl groups. The $ZrO_2$/SAMP-terminated substrate supported cell adhe-sion and spreading (FIG. 17A). NIH3T3 fibroblasts on the 10×10 µm striped pattern spread in alignment with the pattern (FIG. 17B). Because cells were larger than 10 µm wide, they tended to spread over two or more stripes, but in many cases one edge of a cell was aligned with the edge of the pattern. The cells remained aligned with the pattern as they grew to confluence (FIG. 17C).

Figures 18A, 18B, 18C, 18D, 18E, 18F:
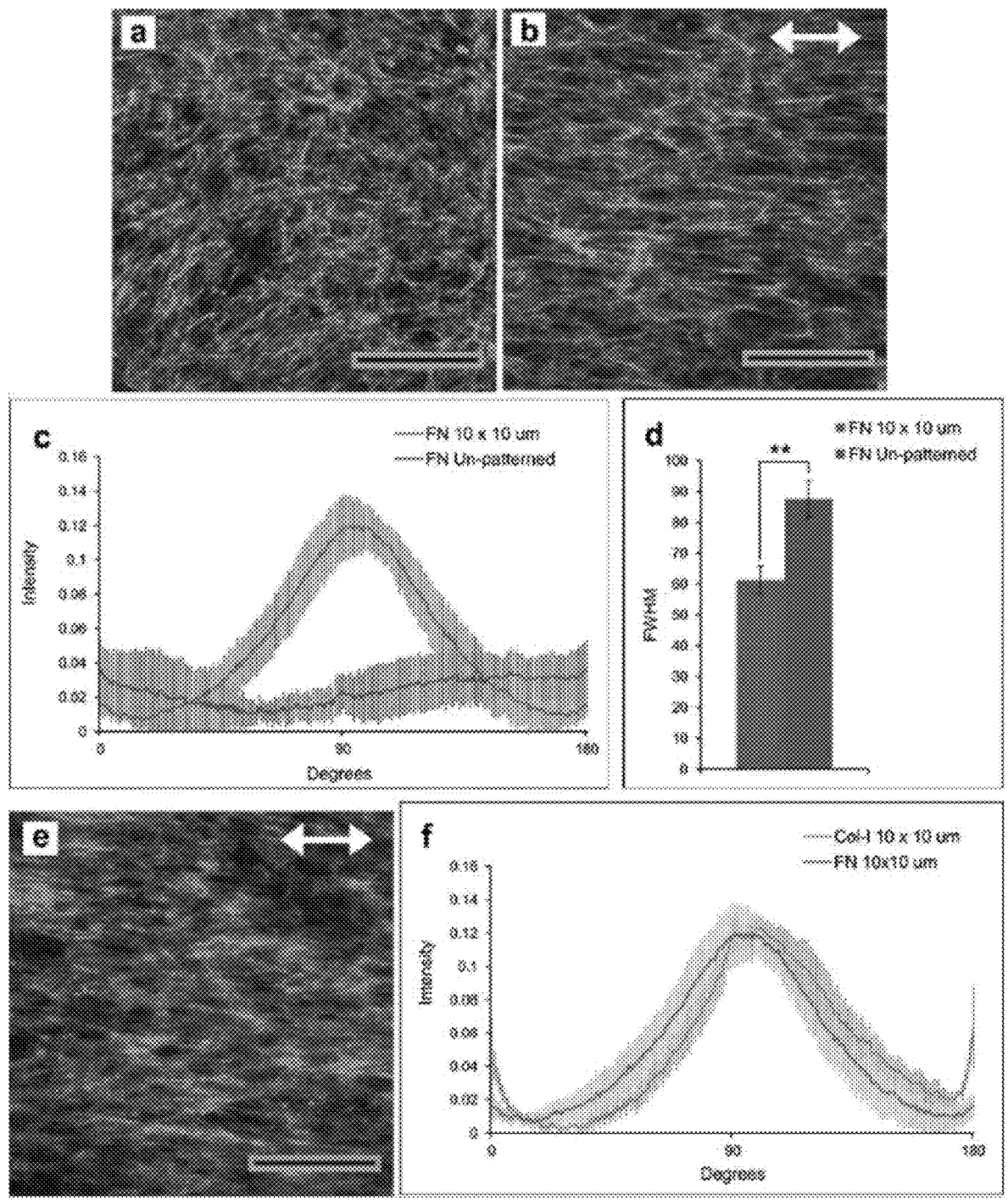

Fibroblasts plated on patterned substrates assemble a natural fibrillar matrix containing fibronectin. During growth of NIH 3T3 fibroblasts for 10 days on 10 µm×10 µm stripe-patterned PET, a robust ECM was assembled. Immunofluorescence detection with anti-fibronectin antibodies showed matrix fibrils that were oriented with the pattern (FIG. 18B) in contrast to the matrix on the unpatterned surface (FIG. 18A). The degree of matrix alignment was quantified by performing two-dimensional fast-Fourier transform analysis (FFT) of the images. The radial summation of pixel intensity in the FFT output for each angle was plotted between 0 to 180°. A peak centered at 90° for the patterned substrates indicated alignment of matrix fibrils parallel to underlying patterned stripes (FIG. 18C). No peak was obvious for matrix on an unpat-terned substrate. The variation in height and shape of the major peak is represented quantitatively by full width-half maximum (FWHM) values. A significantly lower FWHM for the patterned sample indicates higher alignment of fibrils compared to the random fibrils on the unpatterned substrates (FIG. 18D). In addition to fibronectin, the matrix also contained type I collagen fibrils (FIG. 18E) that were co-aligned with the fibronectin fibrils and the pattern (FIG. 18F).

Figures 19A, 19B, 19C, 19D, 19E:
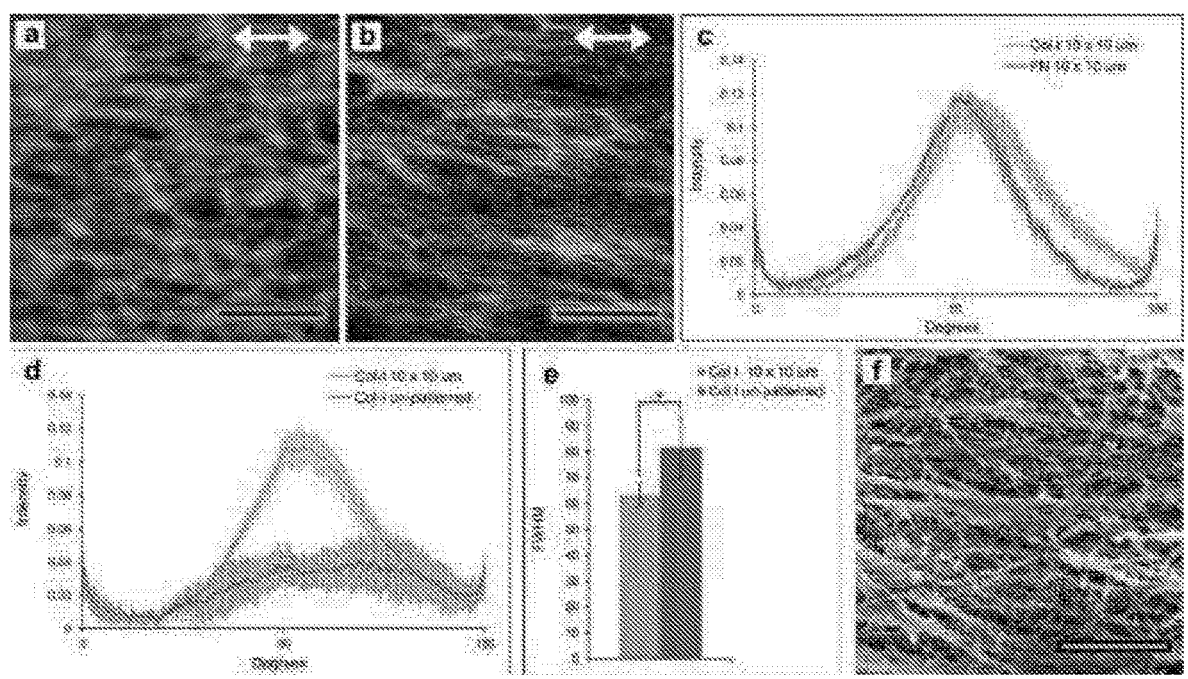

A mild cell-lysis protocol was used to decellularize the matrices that cell-assembled on PET. This procedure maintains the organization and dimensionality of the matrix. Compared to cells on a two-dimensional fibronectin-coated surface, cell activities such as adhesion, migration, and matrix assembly are enhanced when cells are grown on a decellularized three-dimensional ECM as used here. Immunofluorescence and FFT analyses of fibronectin and type I collagen matrix fibrils after decellularization confirmed the matrix remained attached to the PET substrate and fibril alignment was maintained with the pattern (FIGS. 19A-19C). Quantification showed significant alignment of type I collagen fibrils in decellularized matrix on patterned PET compared to unpatterned surfaces (FIG. 19D, E). Analysis of decellularized matrix by scanning electron microscopy (SEM) highlights the density of fibrils and three-dimensionality of the matrix (FIG. 19F).

Example 11

PC12 Culture on Patterned Polymers with Cell-Assembled, Aligned ECM

Figures 20A, 20B, 20C, 20D, 20E, 20F:
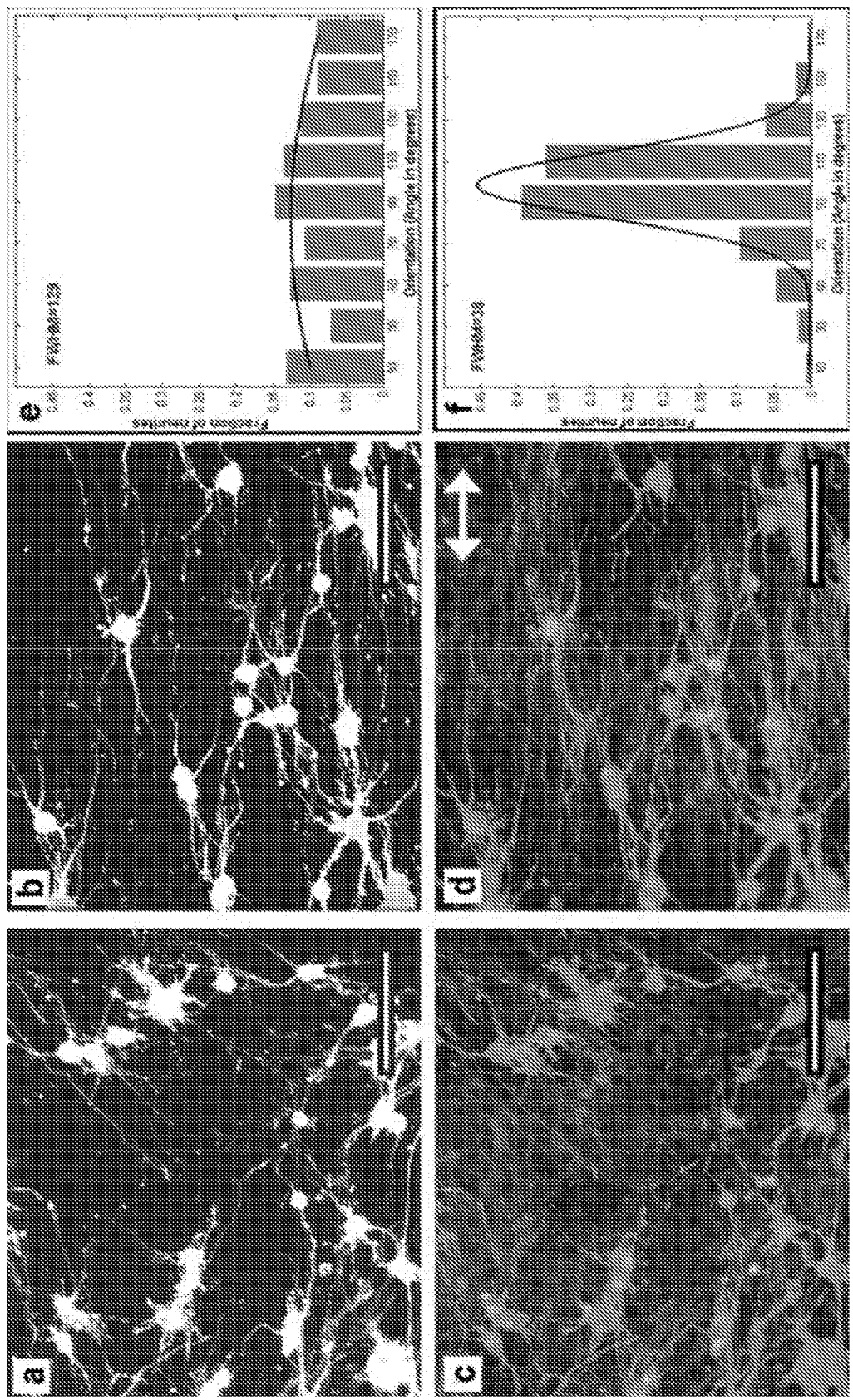

PC12 cells, as surrogates for neurons, were plated on this aligned ECM/PET material of Example 10 and were stimulated for neurite outgrowth that was quantitatively evaluated through directional analysis (FIG. 20). The cells cultured on patterned or unpatterned, decellularized matrix extended neurites, which were visualized by staining the actin cytoskeleton (FIG. 20A, B). Co-staining of matrix fibrils indicated correspondence between the direction of neurite outgrowth and the orientation of fibrils (FIG. 20C, D). Measurements of neurite projection angles relative to the patterned matrix showed the majority of neurites in line with the 10 µm×10 µm pattern (90° peak, FIG. 20F) compared to the lack of a single peak in neurite angles on the unpatterned matrix (FIG. 20E). The aligned orientation of neurites is also reflected in the three-fold decrease in FWHM value compared to the unpatterned substrate (FIG. 20E, F). In this way, the cell-assembled aligned ECM supports neurite outgrowth that is oriented in register with the underlying $ZrO_2$/SAMP-patterned surface. This system therefore provides a platform for studying the effects of alignment in devices used for nerve reconstruction.

Example 12

Radial Glial Cells on Decellularized, Cell-Assembled, Aligned ECM Patterned Polymer Scaffolding Radial glial cells (rat radial glial cell line C6 modified to express GFP obtained from Dr. Martin Grumet at Rutgers University) were plated on the patterned PET material of Example 10, were attached to and were aligned to the patterns and proliferated in alignment with the patterns until reaching confluency on polymers.

The same radial glial cells plated on decellularized ECM adhered in alignment with the matrix fibrils and continue to proliferate for 7-10 days in alignment with ECM until reaching confluency on decellularized patterns. Alignment of cells was quantified by direct measurements of cell angles relative to the patterns (FIG. 21).

Radial glial cells were also plated onto decellularized matrix and cultured for variable periods of time (1-7 days) while maintaining alignment with matrix fibrils. PC12 cells were then plated onto radial glial cell/matrix substrate and co-cultured. Both cell types were observed to attach and grow in register with the aligned matrix on the patterned polymers. Analysis through FFT was done showing that all neurites and glial cells were highly aligned with pattern and ECM direction (FIG. 22). In co-culture with glial cells, neuron cells extend a dense network of aligned neurites spanning the decellularized matrix/polymer substrate.

Example 13

Schwann Cells on Decellularized, Cell-Assembled, Aligned ECM Patterned Polymer Scaffolding Schwann cells (rat neonatal Schwann cells) were plated on the polymer patterns of Example 10 and attach and grow in alignment with patterned stripes. Cells were able to grow over a 10-day period on patterned polymers and retain alignment. Schwann cells plated on cell-assembled, aligned decellularized matrix were attached in alignment with matrix fibrils and proliferate to confluence.

Schwann cells were able to proliferate extensively on decellularized matrix while retaining alignment with matrix fibrils. Schwann cells in co-culture with fibroblasts on the patterned PET of Example 10 grow aligned with patterns and assemble a dense ECM network of fibronectin, collagen, and other ECM proteins produced by fibroblasts and Schwann cells.

Example 14

Neurite Outgrowth and Directionality

Sympathetic cervical ganglia were plated onto substrates to assess neurite outgrowth and directionality. Substrates included a glass coverslip coated with a 10 µg/ml solution of laminin (Laminin), decellularized fibroblast ECM on an unpatterned glass coverslip (Unpatterned ECM), and decellularized aligned ECM on a 20 µm×20 patterned PET surface prepared according to Example 10 (Patterned ECM). See FIGS. 23A and 23B. A single ganglion with extended neurites is shown in each image. The substrate is indicated above the image. In FIG. 23B neurite outgrowth was fitted with an ellipse (lines on images) to determine if neurite extension deviated from circular, i.e., showed directionality. Samples on unpatterned ECM, patterned ECM, and laminin were measured. The aspect ratios (long axis divided by the short axis) displayed in the graph were calculated and averaged for a minimum of 3 samples per condition, and show that the neurites grown on patterned ECM substrates showed significant directionality, i.e., the aspect ratio is significantly different from 1.0 (which would be circular or round).

It will be appreciated by those skilled in the art that changes could be made to the embodiments described above without departing from the broad inventive concept thereof. It is understood, therefore, that this invention is not limited to the particular embodiments or examples disclosed, but it is intended to cover modifications that are within the spirit and scope of the present invention.

What is claimed is:

1. A neural tissue scaffold comprising a base layer and a metal oxide layer, wherein the base layer and the oxide layer comprise a pattern of oxide layer stripes on said base layer, and further comprise a plurality of neural cells on the stripes;
   wherein said oxide layer stripes are deposited across a tissue growth surface of said base layer, with the continuous length of each stripe layer relative to the width being sufficient to direct the outgrowth of neural cells aligned parallel to the lengthwise direction of said stripe, and with the underlying base layer surface exposed therebetween in continuous parallel stripes to provide an alternating pattern of metal oxide and base layer stripes;
   wherein said scaffold further comprises an extracellular matrix (ECM) layer comprising fibronectin assembled by a confluent fibroblast cell layer, where the ECM is oriented across the patterned surface so that ECM fibrils are aligned parallel to the lengthwise-direction of the underlying metal oxide stripes and exposed base layer stripes therebetween;
   wherein the ECM is decellularized;
   wherein said neural cells are attached to the decellularized ECM layer;
   wherein said neural cells are selected from the group consisting of stem cells, oligopotent cells, differentiated neurons, differentiated glial cells and neural crest cells; and
   wherein said neural cells form a confluent monolayer across the ECM layer while maintaining alignment parallel to said alternating pattern of oxide and base layers stripes and ECM.

2. The tissue scaffold of claim 1 further comprising a non-biologic cell adhesive layer disposed on the oxide layer.

3. The tissue scaffold of claim 2 wherein the cell adhesive layer comprises a phosphonate.

4. The tissue scaffold of claim 1 wherein the base layer is a soft polymeric surface where the polymer has a Young's modulus ranging from about 0.2 to about 100 kPa.

5. The tissue scaffold of claim 4 wherein the polymer has a Young's modulus ranging from about 1 to about 30 kPa.

6. The tissue scaffold of claim 1 wherein the base layer is selected from the group consisting of polyesters, polyamides, polylactones, polyacrylamides and polysiloxanes.

7. The tissue scaffold of claim 1 wherein the base layer is selected from the group consisting of silk and collagen.

8. The tissue scaffold of claim 1 wherein the base layer is selected from the group consisting of nylon, polyethylene terephthalate, polycaprolactone fumarate, polyethylene glycol fumarate, and methylene bis acrylamide.

9. The tissue scaffold of claim 1 wherein the stripes are about 5 μm to 100 μm wide and spaced about 5 μm to 100 μm apart.

10. The tissue scaffold of claim 9 wherein the stripes are about 5 μm wide and spaced about 5 μm apart, or about 10 μm wide and spaced about 10 μm apart, or about 20 μm wide and spaced about 20 μm apart, or about 30 μm wide and spaced about 30 μm apart, or about 20 μm wide and spaced about 10 μm apart.

11. The tissue scaffold of claim 1 wherein the metal oxide is zirconium oxide.

12. The tissue scaffold of claim 1 further comprising glial support cells.

13. The tissue scaffold of claim 12 wherein said glial support cells are selected from the group consisting of CNS macroglial cells and PNS macroglial cells.

14. The tissue scaffold of claim 13 wherein said CNS macroglial cells are selected from the group consisting of astrocytes, astrocyte precursor cells, oligodendrocytes and oligodendrocyte precursor cells.

15. The tissue scaffold of claim 13 wherein said PNS macroglial cells are selected from the group consisting of Schwann cells and Schwann precursor cells.

* * * * *